US008323694B2

(12) United States Patent
Hainfeld

(10) Patent No.: US 8,323,694 B2
(45) Date of Patent: Dec. 4, 2012

(54) GOLD NANOPARTICLES FOR SELECTIVE IR HEATING

(75) Inventor: James F. Hainfeld, Shoreham, NY (US)

(73) Assignee: Nanoprobes, Inc., Yaphank, NY (US)

( * ) Notice: Subject to any disclaimer, the term of this patent is extended or adjusted under 35 U.S.C. 154(b) by 1256 days.

(21) Appl. No.: 11/746,278

(22) Filed: May 9, 2007

(65) Prior Publication Data

US 2008/0279946 A1 Nov. 13, 2008

(51) Int. Cl.
*A61K 9/14* (2006.01)
(52) U.S. Cl. .................. 424/489; 424/130.1; 607/100; 977/773
(58) Field of Classification Search ............... 424/489, 424/130.1; 607/100; 977/773
See application file for complete search history.

(56) References Cited

U.S. PATENT DOCUMENTS

| | | | |
|---|---|---|---|
| 4,094,804 A | 6/1978 | Shimoiizaka | |
| 5,360,895 A | 11/1994 | Hainfeld et al. | |
| 5,443,813 A | 8/1995 | Hainfeld | |
| 5,521,289 A | 5/1996 | Hainfeld et al. | |
| 5,690,903 A | 11/1997 | Hainfeld | |
| 6,001,054 A | 12/1999 | Regulla et al. | |
| 6,121,425 A | 9/2000 | Hainfeld et al. | |
| 6,200,598 B1 | 3/2001 | Needham | |
| 6,369,206 B1 | 4/2002 | Leone et al. | |
| 6,423,018 B1 | 7/2002 | Augustine | |
| 6,521,773 B1 | 2/2003 | Hainfeld | |
| 6,534,039 B2 | 3/2003 | Hainfeld | |
| 6,623,430 B1 | 9/2003 | Slayton et al. | |
| 6,645,464 B1 | 11/2003 | Hainfeld | |
| 6,660,058 B1 | 12/2003 | Oh et al. | |
| 6,690,976 B2 | 2/2004 | Fenn et al. | |
| 6,818,199 B1 | 11/2004 | Hainfeld et al. | |
| 6,865,408 B1 | 3/2005 | Abbink et al. | |
| RE38,800 E | 9/2005 | Barbour | |
| 6,953,457 B2 | 10/2005 | Farr et al. | |
| 6,955,639 B2 | 10/2005 | Hainfeld et al. | |
| 6,965,108 B2 | 11/2005 | Bynum et al. | |
| 7,016,717 B2 | 3/2006 | Demos et al. | |
| 7,099,533 B1 | 8/2006 | Chenard | |
| 7,110,807 B2 | 9/2006 | Webber et al. | |
| 7,139,603 B2 | 11/2006 | Chance | |
| 7,610,082 B2 | 10/2009 | Chance | |
| 7,615,340 B2 | 11/2009 | Bamdad | |
| 2005/0020869 A1* | 1/2005 | Hainfeld et al. ............ 600/1 |
| 2005/0130207 A1 | 6/2005 | Hainfeld | |
| 2005/0283071 A1 | 12/2005 | Ripoll | |
| 2007/0031505 A1 | 2/2007 | Roy et al. | |
| 2007/0051202 A1 | 3/2007 | Raghuraman et al. | |
| 2007/0125196 A1 | 6/2007 | Zhong et al. | |
| 2009/0123365 A1 | 5/2009 | Yang et al. | |
| 2009/0239215 A1 | 9/2009 | Derosier et al. | |
| 2010/0003197 A1* | 1/2010 | Bikram ............ 424/9.323 |
| 2011/0034974 A1* | 2/2011 | Munoz Marquez et al. .. 607/101 |

OTHER PUBLICATIONS

Huang X. et al. Plasmonic Photothermal Therapy Using Gold Nanoparticles. Lasers Med Sci 23:217-228, 2008.*
El-Sayed I. et al. Selective Laser Photothermal Therapy of Epithelial Carcinoma Using Anti EGFR Antibody Conjugated Gold Nanoparticles. Cancer Letters 239(1)129-135, Jul. 28, 2006.*
Jain P. et al. Calculated Absorption and Scattering Properties of Gold Nanoparticles of Different Size, Shape and Composition. J Phys Chem B 110:7238-7248, 2006.*
O'Neal D. et al. Photothermal Tumor Ablation in Mice Using Near IR Absorbing Nanoparticles. Cancer Letters 209:171-176, 2004.*
Khlebtsov B. et al. Optical Amplification of Photothermal Therapy with Gold Nanopatciles and Nanoclusters. Nanotechnology 17(20)5167-5179, 2006.*
Cheng et al., "Synthesis and Enzyme-Specific Activation of Carbohydrate-Geldanamycin Conjugates with Potent Anticancer Activity," J. Med. Chem. 48(2):645-652 (2005).
Daniel et al., "Gold Nanoparticles: Assembly, SupramolecularChemistry, Quantam-Size-Related Properties, and Applications toward Biology, Catalysis, and Nanotechnology," Chem. Rev. 104:293-346 (2004).
Moghimi et al., "Long-Circulating and Target-Specific Nanoparticles: Theory to Practice," Pharm. Rev. 53(2):283-318 (2001).
Norman et al., "Ner Infrared Optical Absorption of Gold Nanoparticle Aggregates,"J. Phys. Chem. B. 106:7005-7012 (2002).
O-Neal et al., "Photo-thermal tumor ablation in mice using near infrared-absorbing nanoparticles," Cancer Letters 209:171-176 (2004).
Romberg et al., "Pharmacokinetics of poly(hydroxyethyl-L-asparagine)-coated liposomes is superior over that of PEG-coated liposomes at low lipid dose and upon repeated administration," Biohcim. Biphys. Acta 1768(3):737-743 (2007).
Vieille et al., "Hyperthermophilic Enzymes: Sources, Uses, and Molecular Mechanisms for Thermostability," Microb. Mol. Biol. Rev. 65(1):1-43(2001).
Fan et al., Self-Assembly of Ordered, Robust, Three-Dimensional gold Nanocrystal/Silica Arrays, Science, 2004, 304, pp. 567-571.
Goodman et al., "Surfactant layering on mixed monolayer-protected gold clusters," Colloids and Surfaces B:Biointerfaces 39:119-123 (2004).
Hainfeld et al., "New Frontiers in Gold Labeling," J. or Histochemistry & Cytochemistry, 48, 2000, pp. 471-480.

(Continued)

*Primary Examiner* — Ralph Gitomer
(74) *Attorney, Agent, or Firm* — Wilson Sonsini Goodrich & Rosati

(57) ABSTRACT

Disclosed herein are compositions and methods for increasing the infrared absorptivity of a therapeutic target. Also disclosed are methods for detecting or ablating a therapeutic target that include providing a nanoparticle composition for increasing the infrared absorptivity of the therapeutic target. Subsequently, the therapeutic target having increased infrared absorptivity is exposed to a therapeutically effective dose of infrared irradiation to effect its detection or ablation. In addition, a method is disclosed for treating a subject suffering from a tumor by providing to the tumor a nanoparticle composition for increasing its infrared absorptivity. The tumor having increased infrared absorptivity is then heated by exposing it to a therapeutically effective dose of infrared irradiation.

18 Claims, 11 Drawing Sheets

OTHER PUBLICATIONS

Hainfeld et al., "Ni-NTA-Gold Clusters Target His-Tagged Proteins," J. Structural Biol., 127:185-198 (1999).

Hoeben, Freek J.M. et al., "About Supramolecular Assemblies of π-Conjugated Systems," Chem Rev. 105:1491-1546 (2005).

Hu et al., "Assembly of Nanoparticle-Protein Binding Complexes: From Monomers to Ordered Arrays," Angewandte Chemie, 46, 2007, pp. 5111-5114.

Hu et al., "Protein Assembly Through Site-specific Interactions with Gold Nanoparticles," Mater. Res. Soc. Symp., 951, 2007.

Kabashin et al., "Synthesis of Colloidal Nanoparticles During Femtosecond Laser Ablation of Gold in Water," Journal of Applied Physics, 94 (7941), 2003, pp. 7941-7943.

Love, J.C. et al., "Self-Assembled Monolayers of Thiolates on Metals as a Form of Nanotechnology," Chem. Rev. 105:1103-1169 (2005).

Nakamura et al., "Immobilization of His-Tagged Endoglucanase on Gold via Various Ni-NTA Self-Assembled Monolayers and its Hydrolytic Activity," Macromolecular Bioscience 10:1265-1272 (2010).

Nikoobakht et al., "Evidence for Bilayer Assembly of Cationic Surfactants on the Surface of Gold Nanorods," Langmuir 17:6368-6374 (2001).

Patil et al., "Evidence for Novel Interdigitated Bilayer Formation of Fatty Acids during Three-Dimensional Self-Assembly on Silver Colloidal Particles," J. Am. Chem. Soc. 119:9281-9282 (1997).

Patil et al., "Role of Particle Size in Individual and Competitive Diffusion of Carboxylic Acid Derivatized Colloidal Gold Particles in Thermally Evaporated Fatty Amine Films," Langmuir 15:8197-8206 (1999).

Patil et al., "Surface Derivatization of Colloidal Silver Particles Using Interdigitated Bilayers: a Novel Strategy for Electrostatic Immobilization of Colloidal Particles in Thermally Evaporated Fatty Acid/Fatty Amine Films," Langmuir, 1998, 14, pp. 2707-2711.

Reddy et al., "5nm Gold-Ni-NTA binds His tags," Microsc Microanal., 11(Suppl2), 2005, pp. 1118-1119.

Sastry et al., "Phase transfer of aqueous colloidal gold particles into organic solutions containing fatty amine molecules," Colloids and Surfaces A: Physicochemical and Engineering Aspects 181:255-259 (2001).

Sastry et al., "Langmuir-Blodgett Films of Carboxylic Acid Derivatized Silver Colloidal Particles: Role of Subphase pH on Degree of Cluster Incorporation," J. Phys. Chem. B 101:4954-4958 (1997).

Shen et al., "Bilayer Surfactant Stabilized Magnetic Fluids: Synthesis and Interactions at Interfaces," Langmuir, 1999, 15, pp. 447-453.

Simard, J. et al., "Formation and pH-controlled assembly of amphiphilic gold nanoparticles," Chem. Commun 2000, 1943-1944.

Swami et al., "Formulation of Water-Dispersible Gold Nanoparticles using a Technique Based on Surface-Bound Interdigitated Bilayers," Langmuir, 2003, 19, pp. 1168-1172.

Zhang et al., Didodecyldimethlyammonium Bromide Lipid Bilayer-Protected Gold Nanoparticles: Synthesis, Characterization, and Self-Assembly, Langmuir, 2006,22, pp. 2838-2843.

* cited by examiner

Fig. 4
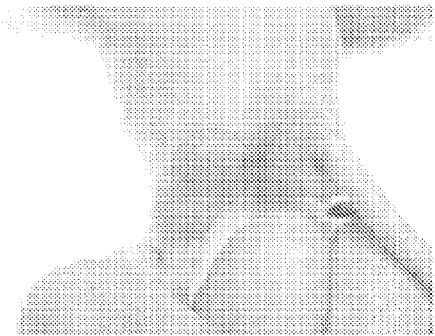
Before Gold Injection
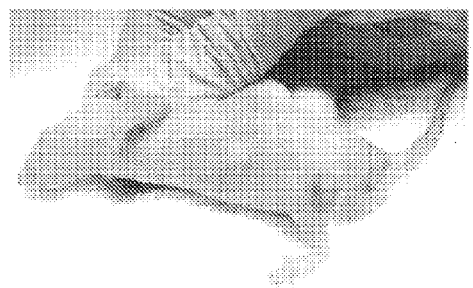
2 hours 20 minutes post-Gold Injection
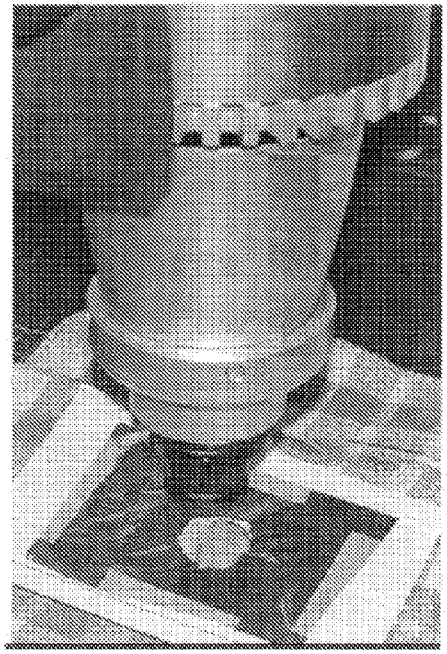
Infrared Irradiation Treatment

Fig. 7
20 days Post-Treatment
Control Animal　　VS　　Gold-Treated Animal
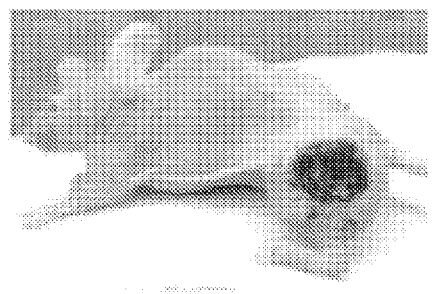
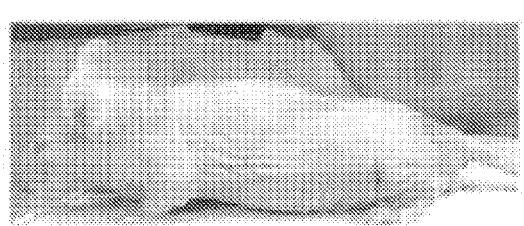
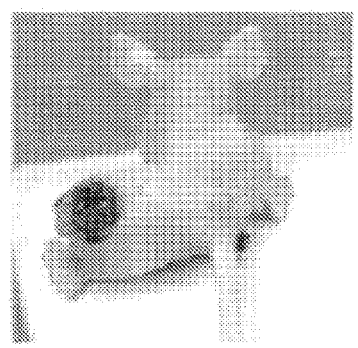
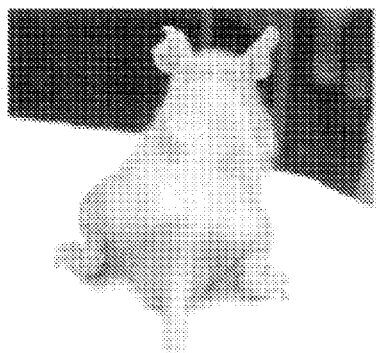

Fig. 9
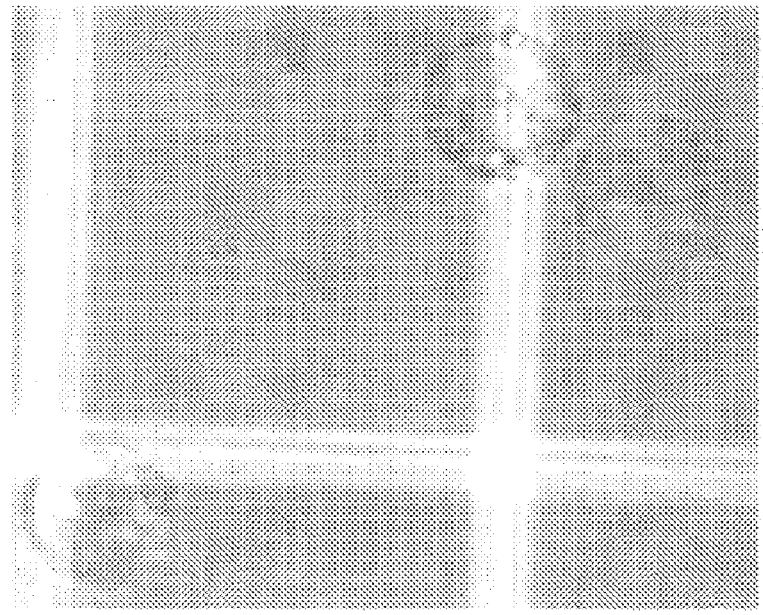
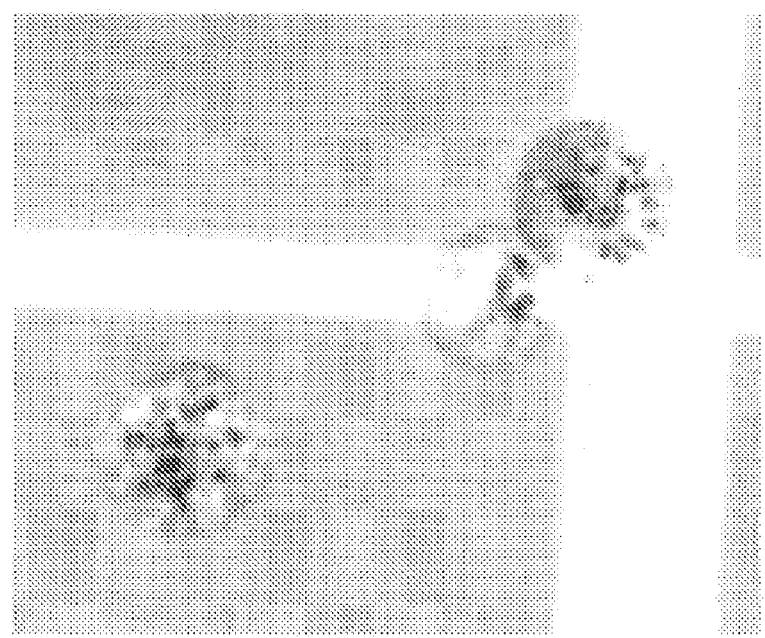

Fig. 10
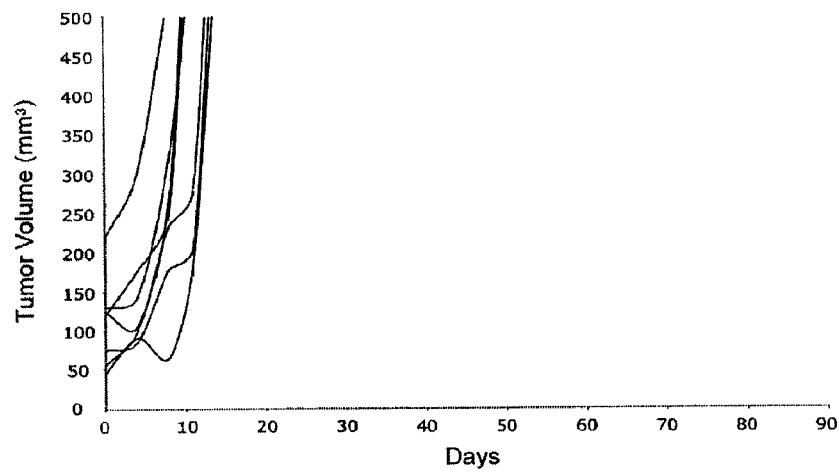
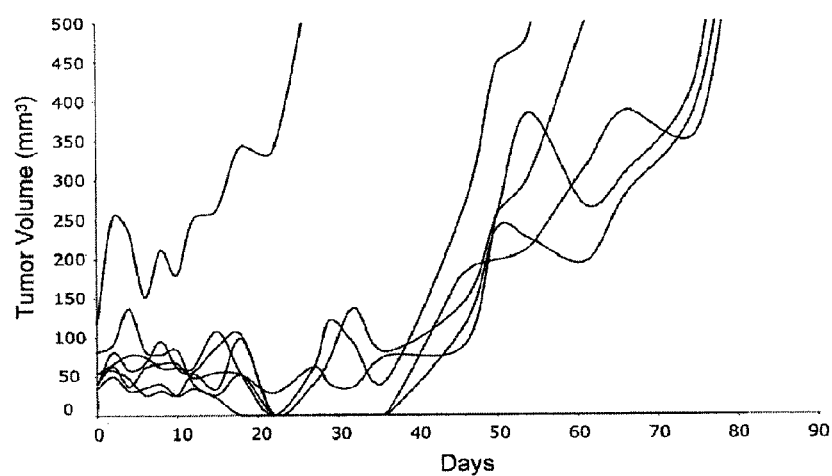
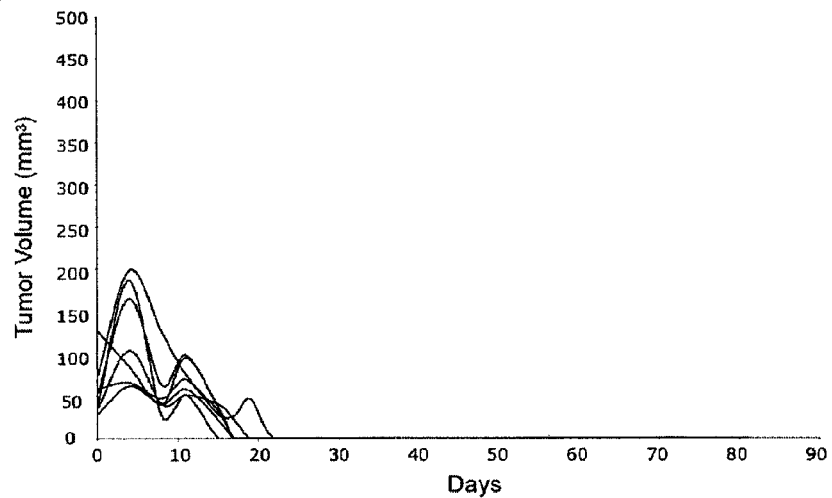

GOLD NANOPARTICLES FOR SELECTIVE IR HEATING

BACKGROUND

Nanotechnology holds great promise for the development of effective diagnostic and therapeutic methods for diseases such as cancer, atherosclerosis, and stroke. In the pursuit of nanotechnology-based therapies, much effort is devoted to the generation and use of biocompatible nanoparticles tailored to have specific physical properties such as high absorptivity for specific wavelengths. For example, "nanoshells" were developed as optically tunable nanoparticles composed of a silica core coated with an ultrathin metallic layer (e.g., gold). The high intrinsic optical absorptivity of nanoshells has been exploited, e.g., to heat-ablate tumors by near-infrared irradiation of nanoshells in vivo.

SUMMARY OF THE INVENTION

Described herein are metal nanoparticle compositions that increase the infrared absorptivity of a therapeutic target, and methods for increasing the infrared absorptivity of a therapeutic target by providing to the therapeutic target an effective amount of the metal nanoparticle compositions as described herein. Also described herein are methods for treating a subject suffering from a tumor by providing to the tumor a composition containing a therapeutically effective amount of metal nanoparticles and then irradiating the tumor with a therapeutically effective dose of infrared radiation.

One aspect described herein relates to a composition containing nanoparticles, where each of the nanoparticles contains one or more metals (e.g., gold, platinum, silver, titanium, palladium, molybdenum, chromium, lead, iron, cobalt, nickel, zinc, tungsten, iridium, osmium, manganese, aluminum, tantalum, bismus, or any combination thereof); one or more of the nanoparticles have optionally bound to them at least one of the following: (i) a stealth group; (ii) a thermophilic enzyme; (iii) a targeting moiety; (iv) a drug or prodrug, and the nanoparticles have an aggregate absorptivity amplification factor of at least about 3 to about 50 (e.g., about 10 to about 50) for infrared wavelength irradiation. An "aggregate absorptivity amplification factor" (A3F) refers to the ratio of the absorptivity of aggregated nanoparticles to the corresponding absorptivity of unaggregated nanoparticles.

In some embodiments, each of the nanoparticles in the composition contains at least two metals. In some embodiments, in each nanoparticle at least about 50% of the core mass is made of one or more metals.

In some embodiments, at least 10% of the nanoparticles have a range of effective diameters from about 0.8 to about 40 nm, e.g., from about 20 to about 40 nm, or from about 10 to about 20 nm. In further embodiments, at least about 20% of the nanoparticles have the aforementioned range of effective diameters, at least about 30% of the nanoparticles have the aforementioned range of effective diameters, at least about 40% of the nanoparticles have the aforementioned range of effective diameters, at least about 50% of the nanoparticles have the aforementioned range of effective diameters, at least about 60% of the nanoparticles have the aforementioned range of effective diameters, at least about 70% of the nanoparticles have the aforementioned range of effective diameters, at least about 80% of the nanoparticles have the aforementioned range of effective diameters, or at least about 90% of the nanoparticles have the aforementioned range of effective diameters.

In one embodiment, one or more of the nanoparticles also have bound to them an antibody (e.g., an anti-tumor associated antigen antibody). In one embodiment, the antibody is an anti-embryocarcinoma antigen antibody. In one embodiment, one or more of the nanoparticles have bound to them antibodies against at least two different epitopes of the same antigen.

In another embodiment, one or more nanoparticles have polyethylene glycol stealth group bound to them.

In another embodiment, one or more of the nanoparticles also have bound to them an anti-cancer agent. In one embodiment the anti-cancer agent is bound to the nanoparticles by a photocleavable linker. In one embodiment, the anti-cancer agent is a photosensitizer agent. In another embodiment, the anti-cancer agent is a radiosensitizer agent.

In another embodiment, one or more of the nanoparticles also have bound to them a thermosensitive liposome containing a therapeutic agent (e.g., an anti-cancer agent or a thrombolytic agent). In one embodiment, the thermosensitive liposome containing the therapeutic agent also contains an infrared fluorophore.

Another aspect described herein relates to increasing the infrared wavelength absorptivity of a therapeutic target by providing to the therapeutic target a therapeutically effective amount of nanoparticles in a patient in need of infrared wavelength ablation or detection of the therapeutic target. Each of the provided nanoparticles contains one or more metals (e.g., gold, platinum, silver, titanium, palladium, molybdenum, chromium, lead, iron, cobalt, nickel, zinc, tungsten, iridium, osmium, manganese, aluminum, tantalum, bismus, or any combination thereof), and the nanoparticles have an aggregate absorptivity amplification factor of at least about 3 to about 50 (e.g., about 10 to about 50) for infrared wavelength irradiation.

In some embodiments, in each nanoparticle at least about 50% (including about 60%, about 70%, about 80%, about 90% and about 100%) of the core mass is made of one or more metals. In other embodiments, each of the nanoparticles consists essentially of one or more metals. In some embodiments, at least 10% of the nanoparticles have a range of of effective diameters from about 1 to about 200 nm, e.g., from about 5 to about 50 nm, or from about 10 to about 20 nm. In further embodiments, at least about 20% of the nanoparticles have the aforementioned range of effective diameters, at least about 30% of the nanoparticles have the aforementioned range of effective diameters, at least about 40% of the nanoparticles have the aforementioned range of effective diameters, at least about 50% of the nanoparticles have the aforementioned range of effective diameters, at least about 60% of the nanoparticles have the aforementioned range of effective diameters, at least about 70% of the nanoparticles have the aforementioned range of effective diameters, at least about 80% of the nanoparticles have the aforementioned range of effective diameters, or at least about 90% of the nanoparticles have the aforementioned range of effective diameters. In other embodiments, one or more of the nanoparticles can have at least one of the following bound to them: (i) an antibody, (ii) a stealth group, (iii) a thermophilic enzyme, (iv) a thermosensitive liposome containing a therapeutic agent; or (v) a therapeutic agent.

A therapeutic target can be, e.g., an atheromatous plaque, a blood clot, or a region of tissue, e.g., a region of degenerated tissue, a region of infected tissue, a region of inflamed tissue, or any combination thereof. In one embodiment, the therapeutic target is a region of retinal tissue. In another embodiment, the therapeutic target is a region of macular tissue. In some embodiments, the therapeutic target is a region of tissue containing vasculature that permits extravasation.

In some embodiments, the nanoparticles are provided to the therapeutic target by parenteral administration to the subject in need. In other embodiments, the nanoparticles are provided directly to the therapeutic target (e.g., by infusion).

The methods described herein can also include exposing a therapeutic target to a dose of infrared irradiation or ionizing radiation after providing the nanoparticles to it. In one embodiment, the therapeutic target is detected based on its absorption of the dose of infrared irradiation. In some embodiments, the dose of infrared irradiation is sufficient to increase a temperature within the therapeutic target (e.g., increasing the temperature to any temperature from about 42° C. to about 1000° C.). In some embodiments, the dose of infrared irradiation is sufficient to kill a population of cells within the therapeutic target, or cause vascular changes, coagulation, protein denaturation, or alter cellular and metabolic precesses, cellular expression and cellular functions.

A further aspect relates to treating a subject suffering from a tumor by providing to the tumor a therapeutically effective amount of nanoparticles and exposing the tumor to a therapeutically effective dose of infrared irradiation. Each of the provided nanoparticles contains one or more metals (e.g., gold); the nanoparticles have an aggregate absorptivity amplification factor of at least about 3 to about 50 (e.g., about 10 to about 50) for infrared wavelength irradiation; and the dose of infrared irradiation is sufficient to elevate a temperature in the tumor (e.g., to any temperature from about 42 to about 500° C.).

In some embodiments, in each nanoparticle at least about 50% (including about 60%, about 70%, about 80%, about 90% and about 100%) of the core mass is made of one or more metals. In other embodiments, each of the nanoparticles consists essentially of one or more metals. In some embodiments, at least 10% of the nanoparticles have a range of of effective diameters from about 1 to about 200 nm, e.g., from about 5 to about 50 nm, or from about 10 to about 20 nm. In other embodiments, one or more of the nanoparticles can have at least one of the following bound to them: (i) an antibody, (ii) a stealth group, (iii) a thermophilic enzyme, (iv) a thermosensitive liposome containing a therapeutic agent, or (iv) a therapeutic agent.

In some embodiments, the tumor contains vasculature that permits extravasation.

In some embodiments, the nanoparticles are provided to the tumor by parenteral administration to the subject in need. In other embodiments, the nanoparticles are provided to the tumor by direct infusion.

Yet another aspect relates to a method for detecting an analyte by contacting the analyte with metal nanoparticles that (i) have an aggregate absorptivity amplication factor of at least about 3 to about 50 for infrared wavelength irradiation; and (ii) have bound to them an analyte binding agent. After binding of the metal nanoparticles to the analyte, the resulting metal nanoparticle aggregates are detected by their increased infrared absorptivity relative to unaggregated metal nanoparticles, whereby the analyte is detected.

In one embodiment, the analyte binding agent is an antibody. In one embodiment the antigen recognized by the antibody is a small molecular weight compound (e.g., a toxin). In one embodiment the small molecular weight compound is a cyanide compound, sarin, soman, tabun, or VC. In another embodiment, the metal nanoparticles have bound to them antibodies that bind to at least two different epitopes of the same antigen.

In some embodiments, the analyte is a polypeptide (e.g., a mammalian polypeptide, an antibody Fc region, a tumor antigen, a pathogenic bacterium antigen, a pathogenic virus antigen, or a cytotoxic protein). In one embodiment, the polypeptide is localized to a viable pathogenic virus or a live pathogenic bacterial cell. In another embodiment, the analyte is a nucleic acid.

In some embodiments, after detection of the analyte a second dose of infrared irradiation is provided that is sufficient to inactivate a pathogenic virus analyte, kill a pathogenic bacterial analyte, or denature a cytotoxic protein analyte.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Unless defined otherwise, all technical and scientific terms used herein have the same meaning as is commonly understood by one of skill in the art to which the claimed subject matter belongs.

All publications and patents mentioned herein are incorporated herein by reference in their entirety for the purpose of describing and disclosing, for example, the constructs and methodologies that are described in the publications, which might be used in connection with the presently described inventions. The publications discussed herein are provided solely for their disclosure prior to the filing date of the present application. Nothing herein is to be construed as an admission that the inventors described herein are not entitled to antedate such disclosure by virtue of prior invention or for any other reason.

As used herein, the term "absorptivity" refers to the ability of a substance to impede transmittance of light of a given wavelength. This property can be described in terms of an extinction coefficient, a reduction in the transmission of light through a sample (regardless of mechanism of action), or by the ability of a substance to absorb light (again, regardless of mechanism).

"Antioxidants" include, for example, butylated hydroxytoluene (BHT), sodium ascorbate, ascorbic acid, sodium metabisulfite and tocopherol. In certain embodiments, antioxidants enhance chemical stability where required.

The term "acceptable" with respect to a formulation, composition or ingredient, as used herein, means having no persistent detrimental effect on the general health of the subject being treated.

As used herein, "amelioration" of the symptoms of a particular disease, disorder or condition by administration of a particular pharmaceutical composition refers to any lessening of severity, delay in onset, slowing of progression, or shortening of duration, whether permanent or temporary, lasting or transient that can be attributed to or associated with administration of the composition.

As used herein, the term "aggregate absorptivity amplification factor" (A3F) refers to the ratio of the absorptivity of aggregated nanoparticles to that of unaggregated nanoparticles.

As used herein, the term "antibody" refers to any polypeptide that contains an immunoglobulin hypervariable (CDR) region antigen binding domain. For example, the antibody can be a monovalent antibody, a divalent antibody, an Fab fragment, a single-chain $F_v$, a monoclonal, or polyclonal antibody.

The term "bound," as used herein refers to one or more associations, interactions, or bonds that are covalent or non-covalent (including ionic bonds, hydrogen bonds, and van der Waals interactions).

The term "carrier," as used herein, refers to relatively non-toxic chemical compounds or agents that facilitate the transport of metal nanoparticles into vasculature, tissues, or cells.

The terms "co-administration" or the like, as used herein, are meant to encompass administration of the selected therapeutic agents to a single patient, and are intended to include treatment regimens in which the agents are administered by the same or different route of administration or at the same or different time.

As used herein, "$EC_{50}$" refers to a dosage, concentration or amount of metal nanoparticles that elicits 50% of a maximal effect that is induced, provoked, or potentiated by the metal nanoparticles.

The term "effective amount," refers to the amount of metal nanoparticles that is required to obtain a therapeutic or diagnostic effect in combination with a therapeutically effective dose of infrared irradiation. A "therapeutically effective amount," as used herein, refers to an amount of metal nanoparticles sufficient to allow detection of a target when the metal nanoparticles are provided to the therapeutic target and the therapeutic target is exposed to a therapeutically effective dose of infrared irradiation or sufficient to relieve to some extent one or more of the pathological indicia associated with the therapeutic target. when exposed to a therapeutically effective dose of infrared irradiation. The result can be reduction and/or alleviation of the signs, symptoms, or causes of a disease, or any other desired alteration of a biological system. For example, an "effective amount" for therapeutic uses is the amount of metal nanoparticles as disclosed herein required to provide a clinically significant decrease in disease symptoms or other pathological indicia without undue adverse side effects. It is understood that "an effective amount" or "a therapeutically effective amount" can vary from subject to subject, due to variation in therapeutic target size, shape, depth, composition, as well as systemic factors such as circulation, metabolism, age, weight, general condition of the subject, the severity of the therapeutic target-associated condition being treated, and the judgment of the prescribing physician.

As used herein, the term "infrared" refers to any wavelength between about 700 to about 1100 nm.

The term "metal nanoparticle," as used herein refers to a nanoparticle that has a core mass which is at least 40% metallic by weight. A metal nanoparticle includes nanoparticles that are composed essentially of metal atoms.

The term "nanoparticle," as used herein, refers to an object of any shape that can be contained in a spherical volume having a diameter of 1000 nm or less (i.e., has an effective diameter of 1000 nm or less).

The term "non-target," as used herein, refers to a biological substrate outside of a volume or surface occupied by a therapeutic target. Such therapeutic targets include, but are not limited to, a tumor, a volume of infected tissue, a volume of degenerated tissue, a volume of inflamed tissue, a blood clot, or a region of plaque.

The term "pharmaceutical combination" as used herein, means a product that results from the mixing or combining of more than one active ingredient and includes both fixed and non-fixed combinations of the active ingredients. The term "fixed combination" means that the active ingredients, e.g. metal nanoparticles described herein and a co-agent, are both administered to a patient simultaneously in the form of a single entity or dosage. The term "non-fixed combination" means that the active ingredients, e.g. metal nanoparticles described herein and a co-agent, are administered to a patient as separate entities either simultaneously, concurrently or sequentially with no specific intervening time limits, wherein such administration provides effective levels of the two agents in the body of the patient. The latter also applies to cocktail therapy, e.g. the administration of three or more active ingredients.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

A "stealth group," refers to a chemical group that, decreases uptake of a metal nanoparticle into liver, or spleen through the reticuloendothelial system, reduces the immunogenicity of a nanoparticle in vivo, or decreases the clearance of the metal nanoparticle from a subject.

A "subject," as referred to herein, can be any verbrate, though preferably a mammal (e.g., a mouse, rat, cat, guinea pig, hamster, rabbit, zebrafish, dog, non-human primate, or human) unless specified otherwise.

The term "thermophilic enzyme" refers to a protein that exhibits peak enzymatic activity within a temperature range of at least about 55 to 105° C.

The term "therapeutic target" refers to a biological substrate (e.g., a tumor, a region of infected tissue, or a region of atheromatous plaque) that is to be acted upon by metal nanoparticles as described herein.

The terms "treat," "treating" or "treatment," as used herein, include alleviating, abating or ameliorating symptoms or pathological indicia of a therapeutic target-associated disease or condition, (e.g., breast tumor-breast cancer) preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Throughout the specification, groups and substituents thereof can be chosen by one skilled in the field to provide stable moieties and compositions. Other features, objects, and advantages will be apparent from the description and from the claims. The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 4 is a set of three representative photos showing: a nude mouse bearing a LS174 cell tumor in its left hind leg (top left panel); the same mouse 2 hours and 20 minutes after intravenous injection of 15 nm gold nanoparticles conjugated to an anti-carcinoembryoma antigen antibody (top right panel); and the experimental configuration for infrared irradiation of the tumor in the mouse after the gold nanoparticle injection (bottom panel).

FIG. 7 is a set of four representative photographs showing a tumor-bearing control mouse (top and bottom left panels) and a gold nanoparticle-treated mouse 20 days after receiving an infrared irradiation treatment.

FIG. 9 is a set of representative photomicrographs of A431 human carcinoma cells cultured in the presence (bottom panel) or absence (top panel) of 15 nm gold nanoparticles conjugated to an anti-EGFR antibody. Note the dark black granules of gold accumulated within the cells incubated with the gold nanoparticles.

FIG. 10 is a set of representative graphs of tumor size versus days after hyperthermia treatment (44° C. for 20 min, top panel), radiation treatment (30 Gy, middle panel), or combined hyperthermia and radiation treatment (bottom panel). Tumor volumes for seven animals are plotted separately in each graph.

DETAILED DESCRIPTION

Figure 1:
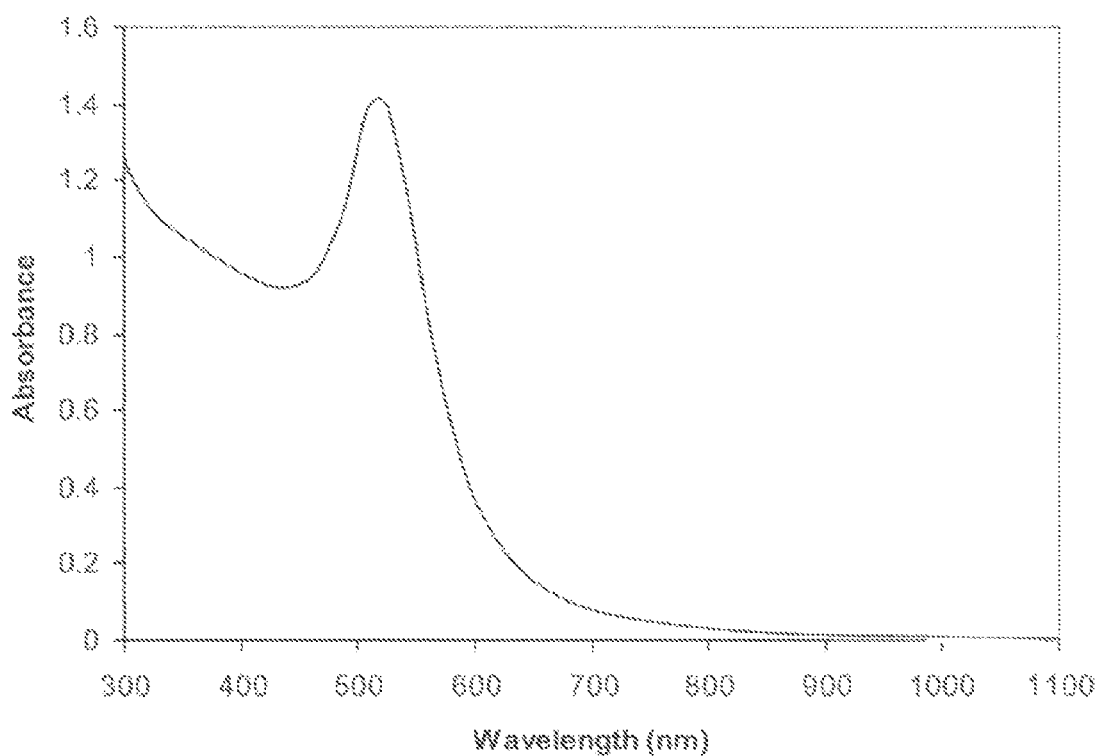
FIG. 1 is a representative absorbance spectrum of unaggregated 15 nm gold nanoparticles for wavelengths from 300-1100 nm.

There is a continuing need for compositions and methods for the detection and treatment of therapeutic targets. Here we describe an approach to detecting and treating therapeutic targets: small gold nanoparticles, which hardly absorb infrared (IR), to a therapeutic target (e.g., a tumor) where they are biologically aggregated and thereby converted within the target locus to IR absorbers. Infrared irradiation can then be used to selectively heat the aggregated gold nanoparticles to detect or ablate the therapeutic target. Importantly, infrared treatment can completely eradicate a therapeutic target while sparing surrounding normal tissue. Accordingly, metal nanoparticle compositions and methods are described herein for differentially increasing the infrared absorptivity of a therapeutic target relative to that of a non-target (e.g., surrounding tissue) in vivo. Also described herein are methods for treating a subject suffering from a tumor by providing to the tumor a plurality of metal nanoparticles that aggregate in the tumor and then heat-ablating the tumor by infrared irradiation of the aggregated nanoparticles. Also described herein are methods for detecting an analyte of interest (e.g., a polypeptide) by contacting the analyte with metal nanoparticles bearing an analyte-binding reagent (e.g., an antibody against the analyte), whereby the analyte-binding metal nanoparticles cluster and aggregate in a complex with the analyte. Analyte-metal nanoparticle complexes are then detected by the increased infrared absorptivity of the aggregated metal nanoparticles.

The methods described herein include providing to a therapeutic target (e.g., a tumor) metal nanoparticles in a therapeutically effective amount.

Various gold nanoparticles, such as nanoshells (~130 nm), nanorods (>50 nm), and large solid spheres (>50-100 nm), absorb infrared (IR) and could be used for hyperthermia therapy. Untargeted nanoshells have efficacy in mice in small (~4 mm thick) tumors.

We have found that small gold particles are well targeted and converted. Small gold particles (e.g., 15 nm) have far better tumor penetration than 130 nm nanoshells or 100 nm nanorods, but have been ignored due to their poor IR absorption. We have discovered, however, that when the small gold particles are targeted to a tumor, their proximity allows them to act in concert such that the aggregate resonates and absorbs at longer wavelengths, particularly in the infrared spectrum.

The increase in IR absorption is on the order of a factor of 20. This localized increase in absorption due to nanoparticle aggregation permits focused heating of a therapeutic target without heating non-target tissue outside of the nanoparticle aggregate volume.

Small metal nanoparticles (about 0.8 to 50 nm in diameter) absorb poorly in the infrared range (~750-1100 nm), which is considered to be a range well suited for in vivo applications. Thus, such metal nanoparticles have generally been deemed inadequate for in vivo infrared photo-diagnostic and photo-therapeutic (e.g., thermal ablation) methods. Indeed, workers in the field have developed optically-tuned "nanoshells," (which are not metal nanoparticles as defined herein) in part, to overcome this limitation. See, e.g., O'neal et al. (2004), *Cancer Letters*, 209:171-176.

Without being bound by theory, the methods described herein exploit the differential infrared absorptivity of metal nanoparticle aggregates versus unaggregated metal nanoparticles to selectively increase the infrared absorptivity of a therapeutic target (e.g., a tumor) or an analyte (e.g., a cytotoxic protein). Metal nanoparticles are aggregated in a therapeutic target and can subsequently be detected in vivo by exposing the therapeutic target to infrared irradiation coupled with infrared detection. Alternatively, or in addition, the aggregated metal nanoparticles localized to the therapeutic target can be utilized in several photothermal therapeutic applications (e.g., thermal ablation of a tumor tissue). Unaggregated metal nanoparticles, i.e., those located outside of the therapeutic target area do not absorb infrared energy efficiently and therefore will not damage non-target tissues. In contrast, individual nanoparticles made of materials that have high intrinsic infrared absorptivity (e.g., nanoshells) can absorb infrared energy efficiently even outside of the therapeutic target, and can therefore damage non-target tissues.

Thus, the differential infrared absorptivity of metal nanoparticle aggregates is a significant therapeutic advantage of metal nanoparticles over nanoparticles "tuned" for infrared absorption.

Accordingly, the metal nanoparticle compositions and methods described herein can be used to drive a localized increase in the infrared absorptivity of a target (e.g., a therapeutic target) or analyte. Inducing localized increases in infrared absorptivity is useful in a very wide range of applications which include, but are not limited to, detection, and optionally, thermal ablation of tumors, photothermal release of therapeutic agents, detection, and optionally, thermal degradation of analytes (e.g., pathogens and toxins), tissue welding, non-ablative heating, e.g., to promote wound healing, thermal initiation of polymerization, infrared detection of materials that cause aggregation of metal nanoparticles, such as salt concentration, solvents compostions, (such as ethanol content), binding of metal surface ligand to a target substance on other materials, cells, or other complementary metal particles (such as nucleic acid hybridization, antibody, drug, or ligand binding), optical coherence tomography, drug delivery, surface-enhanced Raman spectroscopy, fluorescent enhancement, photocatalysis, nanowire synthesis, contrast agent imaging, generation of molecular sensors, generation of immunosensors, and construction of nanoparticle alloys.

Methods for Increasing Infrared Absorptivity In Vivo

In some embodiments, the metal nanoparticles and metal particle compositions described herein are used to differentially increase the infrared absorptivity of a therapeutic target above that of a non-target in a subject in need of detection or ablation of a therapeutic target in vivo. In various embodiments, a therapeutically effective amount of metal nanoparticles is provided to a therapeutic target, where they aggregate and effect a local increase in infrared absorptivity.

In some embodiments, the therapeutic target is a benign or malignant tumor, e.g., a breast tumor (breast cancer), squamous cell papilloma, a squamous cell carcinoma, a basal cell tumor, a basal cell carcinoma, a transitional cell papilloma, a transitional cell carcinoma, a glandular epithelium adenoma, a melanocytes glomus tumor, a melanocytic nevus, a malignant melanoma, a fibroma, a fibrosacroma, an adenocarcinoma, a gastrinoma, a malignant gastrinoma, an oncocytoma, a cholangiocellular adenoma, a cholangiocellular carcinoma, a hepatocellular adenoma, a hepatocellular carcinoma, a renal tubular adenoma, a renal cell carcinoma (Grawitz tumor), a myxoma, a myxosarcoma, a lipoma, a liposarcoma, a leiomyoma, a leiomyosarcoma, a rhabdomyoma, rhabdomyosarcoma, a benign teratoma, a malignant teratoma, a hemangioma, a hemangiosarcoma, a Kaposi sarcoma, a lymphangioma, a lymphangiosarcoma, an osteoma, an osteosarcoma, an osteogenic sarcoma, a cartilage chondroma, a chondrosarcoma, a meninges meningioma, a malignant meningioma, oligoastrocytoma, an ependymoma, an astrocytoma, a pilocytic astrocytoma, a glioblastoma multiform, an oligodendroglioma, a neuroblastoma, a schwanoma, a retinoblastoma, or a neurofibroma. Other types of tumors are have been described, e.g., the "International Classification of Diseases for Oncology," 3rd Edition, International Association of Cancer Registries.

In one embodiment, the therapeutic target is a circulating tumor cell.

In another embodiment, the therapeutic target is a circulating tumor microembolus. See, e.g., Paterlini-Brechot et al. (2007), Canc. Lett., February 19 (E-publication ahead of print).

In other embodiments, the therapeutic target is a region of atheromatous plaque.

In yet other embodiments, the therapeutic target is a region of degenerated tissue (e.g., retinal tissue such as in macular degeneration and diabetic retinopathy), a region of infected tissue, a region of inflamed tissue, or a region of normal tissue. In one embodiment, the therapeutic target is a site where new blood vessels are forming.

In another embodiment, the therapeutic target is a blood clot.

Symptoms, diagnostic tests, and prognostic tests for each of the above-mentioned therapeutic targets and their associated pathologies are known. See, e.g., "Harrison's Principles of Internal Medicine©," 16th ed., 2004, The McGraw-Hill Companies, Inc.

In some embodiments, the metal nanoparticles used in the methods described herein are functionalized with an antibody against the therapeutic target, e.g., an antibody containing a tumor antigen binding domain.

In further embodiments, the metal nanoparticles used in the methods described herein are functionalized with a stealth group, e.g., polyethylene glycol, which can reduce uptake of the metal nanoparticles in liver and spleen through the reticuloendothelial system.

In some embodiments, metal nanoparticles are provided to a therapeutic target, in a subject in need, by parenteral administration of a metal nanoparticle composition described herein. This route is preferred where the vasculature in or near the therapeutic target permits extravasation of the metal nanoparticles into the therapeutic target. Extravasation often occurs in pathologies that exhibit leaky vasculature, e.g., many tumors and inflamed tissues. See, e.g., Moghimi et al. (2001), *Pharm. Rev.*, 53(2):283-318.

In other embodiments, the metal nanoparticles are provided directly to the therapeutic target, e.g., by injection into or in close proximity to the therapeutic target. For example, a composition containing the metal nanoparticles can be introduced into the therapeutic target through a catheter or a syringe needle.

In a variety of embodiments, a therapeutic target that has been provided a plurality of the metal nanoparticles described herein is also exposed to a dose of infrared radiation.

In some embodiments, the dose of infrared radiation is used to detect the therapeutic target, based on its increased infrared absorptivity. Methods for detecting infrared absorption in tissue are known. See, e.g., U.S. Pat. Nos. 7,139,603, 7,016,717, or 6,965,108.

In other embodiments, the therapeutic target, in the presence of metal nanoparticle aggregates is provided with a dose of infrared radiation sufficient to increase its temperature to any temperature from about 42 to about 90° C. for a period of time ranging anywhere from about 10 seconds up to about 60 minutes.

In some embodiments, the temperature in the therapeutic target is increased to a level sufficient to ablate the therapeutic target or a portion thereof. Where the therapeutic target is a tissue, ablation of the therapeutic target refers to inducing cell death, by any mechanism (e.g., apoptosis or necrosis) in at least a population of cells within the therapeutic target. Cell death may occur during exposure of the therapeutic target to the dose of infrared radiation or immediately thereafter, or, in some cases, may occur after a longer period of time following the dose, e.g., any time between about 15 minutes to about three weeks following the dose of infrared radiation.

In some embodiments, the increased temperature of a therapeutic target is maintained within a desired range by measuring a temperature in or in close proximity to the therapeutic target during infrared irradiation of the target, and regulating the dose of infrared radiation accordingly. For example, the source of infrared radiation can be turned on and off manually according to the measured temperature. Alternatively, a thermostat feedback loop can be set up between the temperature sensor (e.g., a thermocouple) and the source of infrared radiation. Methods and devices for thermostatic control of tissue heating are known. See, e.g., U.S. Pat. Nos. 6,865,408 or 6,423,018.

In some embodiments, the infrared radiation source is an infrared lamp capable of delivering an infrared dose rate of about 0.1-10 watts/cm$^2$. Such devices are widely available commercially, e.g., the hydrosun® Irradiator is available from Hydrosun Medizintechnik (Müllheim, Germany). In other embodiments, the infrared radiation source is an infrared laser capable of delivering an infrared dose rate of about 0.1-10 watts/cm$^2$. Infrared lasers for medical applications are widely available, e.g., from Power Technology, Inc. (Alexander, Ariz.).

Where a therapeutic target is located no more than about 3 cm away from the subject's body surface (e.g., a malignant melanoma), the dose of infrared radiation can be provided externally, i.e. to the subject's skin surface by conventional means. Where the therapeutic target is located at a depth greater than about 3 cm away from the subject's body surface (e.g., a liver tumor), there are several alternative methods for delivering an effective dose of infrared irradiation to the therapeutic target. For example, the therapeutic target can be exposed to infrared irradiation intraoperatively. In other embodiments, a deep therapeutic target is exposed to infrared irradiation by means of an infrared-transmitting optical fiber coupled to a infrared radiation source (e.g., an infrared laser) as described in, e.g., U.S. Pat. No. 6,953,457. Fiber optic delivery of infrared irradiation can be used in combination with, e.g., endoscopy, laparoscopy, or under image guidance by x-ray, MRI, or other imaging methods.

In some embodiments, the dose of infrared irradiation is emitted from various locations relative to the therapeutic target. In one embodiment, tomographic infrared irradiation (tomo-IR) is used. In tomo-IR, a collimated IR source (like a pencil beam, or other shape if desirable) is rotated around the body (or the body rotated), but the beam remains focused on an internal volume. In this way, the dose is spread out over the skin and deeper regions, but the dose is additive in the focus volume. Thus, tomo-IR permits a higher cumulative dose of irradiation, relative to unidirectional irradiation, to be administered to the therapeutic target volume without increasing damage to surrounding tissue. In another embodiment, the infrared irradiation is intensity modulated. Intensity modulated IR is similar in principle to tomo-IR, but the infrared beam may be changed in intensity as it rotates relative to the body, and the shape of the incident beam may also be changed during rotation with shutters or by other means. This has the effect that the shape of the target volume does not have to be spherical, but may be designed and shaped such that it fits the tumor shape better and avoids irradiation of sensitive nearby tissues, such as the optic nerve.

In a further embodiment, multiple source infrared irradiation (multi-IR) is used to administer the dose of infrared radiation to the therapeutic target. In multi-IR, many IR sources are placed around a sphere, circle, or other shape, such that no rotation of the IR source or target is necessary, and all the IR beams focus on an internal spot. This design eliminates the need for motion control. For example, a helmet with many IR sources could be used to focus many IR beams on a brain tumor. Many separate IR sources can be used, or, alternatively, a single IR source can be used if it is split into a number of individual beams. For example, an IR beam can be split into multiple beams by illuminating a bundle of fiber optic light pipes that are then separated and routed to the multibeam apparatus positions such that they all focus on the therapeutic target volume, but from different angles. Methods for tomo-IR, intensity modulated IR, and multi-IR are described in, e.g., U.S. Pat. No. RE38,800 and U.S. Pat. No. 7,110,807; and U.S. patent application Ser. Nos. 11/003,936 and 10/982,542.

In some embodiments, a dose of infrared radiation is provided as one or more short (e.g., $10^{-4}$-$10^{-12}$ second) pulses rather than as a continuous illumination. IR absorbing aggregates of nanoparticles heat more rapidly than tissue. Indeed, high intensity pulses of IR can increase the temperature of the nanoparticle aggregates to 500-1000° C. However, as this heat is highly localized to the volume of the nanoparticle aggregates, it dissipates rapidly after the IR exposure, and therefore bulk heating is minimal. Methods and devices for delivery of high intensity pulsed IR radiation are known. See, e.g, U.S. Pat. No. 7,099,533.

Pulsed infrared irradiation mode is useful in a number of embodiments of the methods described herein. After the nanoparticle aggregates absorb pulsed IR radiation, they reach a high temperature for a brief instant and then emit a pulse of heat. This heat radiation pulse travels back through the tissue and can be detected. In some embodiments, detection of the aggregate-emitted heat pulse is achieved by setting the detection time window to have a specific phase interval relative to the IR pulse. Phasing the detection window avoids a loss of signal due to averaging of the nanoparticle aggregate temperature signal with background temperature values as the nanoparticle aggregate cools. In one embodiment, the IR pulse width and subsequent measurement time are carried out between $10^{-6}$ and $10^{-12}$ seconds, and the IR wavelengths are in the 700-900 nm range. In some embodiments, the emitted radiation from the heated nanoparticle is measured at wavelengths ranging from 700 nm to 10 microns. In one embodiment, noise in the measurement of the emitted radiation is reduced further by averaging signals induced by many IR pulses. For example, for a picosecond pulse of IR followed by a picosecond measurement with a duty cycle of 10 picoseconds, averaging in 10 seconds would reduce the noise by a factor of one million. The net result of using pulsed irradiation and synchronized pulse-window detection leads to a very large increase in sensitivity in the detection of deep therapeutic targets (e.g., colon tumors).

In another embodiment, an IR pulse is delivered to metal nanoparticle aggregates to heat them above 100° C. thus causing the aqueous layer surrounding the nanoparticle to vaporize in a small region. The small gaseous bubbles can serve as an ultrasound contrast medium for imaging. The gaseous bubbles can further be utilized for additional heating by application of ultrasound energy.

In another set of embodiments, pulsed IR irradiation is used to achieve highly localized biological alterations and damage close to nanoparticle aggregates without causing bulk heating. For example, metal nanoparticles functionalized with an antibody to a particular pathogen (e.g., a pathogenic bacterium, pathogenic virus, or a cytotoxic protein) or cell type (e.g., a melanoma cell), thereby permitting highly localized IR-induced killing or inactivation of the pathogen. In one embodiment, a viral infection is treated in by administering nanoparticles coated with an anti-viral antigen antibody, and subsequently exposing a region of skin to pulsed IR over a period of time to inactivate circulating virus as it passes through the IR-exposed region.

In another embodiment, metal nanoparticles are functionalized with an antibody against an antigen found on the surface of circulating tumor cells or circulating tumor microemboli (e.g., EpCAM). A subject suspected of or shown to have circulating tumor cells or microemboli is then administered the anti-tumor antigen bearing nanoparticles. Subsequently, the circulating tumor cells or microemboli are killed by exposing a region of the subject's skin to pulsed IR over a period of time is used to kill circulating tumor cells or circulating tumor microemboli. In various embodiments, pulsed IR exposure is used to treat, e.g., HIV infections, lymphomas, leukemias, and other blood-borne diseases.

In view of the disclosure provided herein, nanoparticles capable of absorbing IR radiation, notwithstanding their A3F properties, can be utilized for their IR irradiation modalities and applications.

Ex Vivo Applications

The metal nanoparticle compositions described herein are useful in a number of Ex Vivo applications. In some embodiments, metal nanoparticles functionalized with an analyte binding reagent are used to detect the presence of an analyte in a sample (e.g., a tissue sample, a blood sample, an air sample, a food sample, or a water sample). In the presence of the analyte the functionalized metal nanoparticles form aggregates that are detectable by virtue of their higher IR absorptivity relative to individual nanoparticles as described herein. In one embodiment, the analyte binding reagent is an antibody. In embodiments where the analyte to be detected is immobilized (e.g., a cell surface antigen), localization of the antigen molecules is sufficient to promote clustering of the antibody-bearing metal nanoparticles and aggregate formation. In embodiments where the antigen to be detected is in solution, the metal nanoparticles bear antibodies that recognize at least two different epitopes of the antigen, thereby permitting antibody crosslinking of the metal nanoparticles to form aggregates.

In some embodiments, the analyte is a polypeptide. Examples of polypeptide analytes include, but are not limited to, tumor-associated antigens (e.g., prostate-specific antigen, carcinoembryonic antigen, calcitonin, cancer antigen, 19-9, cancer antigen-125, cancer antigen 72-4, Her-1/EGFR, Her-2/Neu, alpha-fetoprotein, S-100 antigen, or TA-90 antigen); pathogenic virus antigens (e.g., antigens from HIV, herpes virus, smallpox virus, influenza virus, avian influenza A virus, or adenovirus); pathogenic bacterial antigens (e.g., polypeptide antigens from *Bacillus anthracis*, *Francisella tularensis*, *Salmonella typhimurium*, *Vibrio cholerae*, *Yersinia pestis*, *Streptococcus*, *Pneumococcus*, *Clostridium botulinum*, or *E. coli* serotype O157:H7); cytotoxic proteins (e.g., anthrax toxin protective antigen, anthrax toxin edema factor, anthrax toxin lethal factor, ricin A chain, or ricin B chain, botulinum toxin type A, or botulinum toxin type B); or an antibody Fc region (e.g., the Fc region of an antibody bound to its target antigen). In some embodiments, the polypeptide analyte is localized to a cell (e.g., a live cell) or a virus in the sample.

In other embodiments, the analyte is a nucleic acid (e.g., an oligonucleotide, an mRNA, a cDNA, or a genomic DNA).

In other embodiments, the analyte is a low molecular weight compound, e.g., a toxin. Examples of toxins include, but are not limited to chemical weapon toxins such as, cyanide compounds, sarin, soman, tabun, or VX.

In some embodiments, formation of antigen-bound metal nanoparticle aggregates can, optionally, also be exploited to heat an antigen or an antigen bearer (e.g., a pathogenic bacterium) by providing an additional dose of infrared radiation as described herein. In one embodiment, the heating is sufficient to kill a bacterial cell. In another embodiment, the heating is sufficient to inactivate a virus. In another embodiment, the heating is sufficient to denature a protein.

Examples of Metal Nanoparticles

Methods for producing metal nanoparticles are known. See, e.g., Daniel et al. (2004), Chem. Rev., 104:293-346. Nanoparticles suitable for the compositions and methods described herein are biocompatible metal nanoparticles having a high infrared aggregate absorptivity amplification factor (A3F), i.e., a high A3F for any wavelength ranging from about 700 to about 1100 nm. A3F is defined herein as the ratio of the absorptivity of aggregated nanoparticles for a given wavelength to that of unaggregated nanoparticles for the given wavelength. Suitable metal nanoparticles include those having an infrared A3F of at least 3 to about 10, 15, 20, 25, 30, 35, 40, 45, 50, 55, or about 60. The infrared A3F of metal nanoparticles can be determined by measuring the infrared absorbance spectrum of the unaggregated nanoparticles in solution, e.g., in distilled water, and then aggregating the particles (e.g., in the presence of 300 mM NaCl) and measuring the infrared extinction spectrum of the nanoparticle aggregate solution. See, e.g., Norman et al. (2002), *J. Phys. Chem B*, 106:7005-7012.

In some embodiments, the metal nanoparticles have a core that is made of at least about 50% metal (i.e., any percent from 50 to 100%) by weight.

Suitable metals include, e.g., gold, platinum, silver, titanium, palladium, Molybdenum, Chromium, lead, Iron, Cobalt, Nickel, Zinc, Tungsten, Iridium, Osmium, Manganese, Aluminum, Tantalum, Bismuth, or any combination thereof.

In some embodiments, compositions provided herein include metal nanoparticles that have effective diameters of about 0.8 nm up to about 10 nm, about 20 nm, about 30 nm, about 40 nm, about 50 nm, about 60 nm, about 70 nm, about 80 nm, about 90 nm, about 100 nm, about 200 nm, about 300 nm, about 400 nm, about 500 nm, about 600 nm, about 700 nm, about 800 nm, or up to about 900 nm. In some embodiments, compositions provided herein include metal nanoparticles that have effective diameters of about 0.5 nm up to about 200 nm. In other embodiments, compositions provided herein include metal nanoparticles that have effective diameters of about 1 nm up to about 100 nm. In some other embodiments, compositions provided herein include metal nanoparticles that have effective diameters of about 1 nm up to about 40 nm. In some embodiments, compositions provided herein include metal nanoparticles that have effective diameters of about 1 nm, about 2 nm, about 3 nm, about 4 nm, about 5 nm, about 10 nm, about 15 nm, about 20 nm, about 25 nm, about 30 nm, about 35 nm, about 40 nm, about 45 nm, about 50 nm, about 55 nm, or about 60 nm.

Overall, this approach also has the advantage that the activation and/or release only occurs where the irradiation is directed. This is in contrast to drugs that are typically administered systemically which leads to toxicity in other tissues and organs.

In some embodiments, the metal nanoparticles are functionalized with a therapeutic agent (e.g., an anticancer agent or a thrombolytic agent) bound to the nanoparticles through a photocleavable linker. Photocleavable linkers are linkers that are cleaved upon exposure to light (see, e.g., Goldmacher et al. (1992) *Bioconj. Chem.* 3:104-107) thereby releasing the targeted agent (e.g., a linked anti-cancer agent) upon exposure to light. Photocleavable linkers that are cleaved upon exposure to light are known. See, e.g., Ottl et al. (1998), *Bioconjug. Chem.*, 2:143-151; Ottl (1998), *Methods Enzymol* 291:155-175; Yan et al (2004), *Bioconjug. Chem.*, 15(5): 1030-1036; and Kim et al. (2006), *Bioorg Med Chem Lett.*, 16(15):4007-4010.

In some embodiments, the metal nanoparticles are functionalized so as to associate with their surface an antibody, a stealth group, a thermosensitive liposome, a peptide, a polypeptide (e.g., a thermophilic enzyme), a nucleic acid, a drug, an organic moiety, a fluorophore, a carbohydrate, a lipid, or any combination thereof. Each of these can be associated either directly with the surface of the metal nanoparticle (e.g., through a sulfhydryl moiety) or indirectly through a bifunctional crosslinker or organic shell coating the surface of the metal nanoparticle. Methods for derivatizing metal nanoparticles are known. See, e.g., Daniel et al. (2004), *Chem. Rev.*, 104:293-346. See also U.S. patent application Ser. Nos. 11/271,392 and 11/549,071.

In some embodiments, the metal nanoparticles are functionalized with an antibody that binds, e.g., a tumor or tumor-associated antigen, including cancer-germ cell (CG) antigens (MAGE, NY-ESO-1), mutational antigens (MUM-1, p53, CDK-4), over-expressed self-antigens (p53, HER2/NEU), viral antigens (from Papilloma Virus, Epstein-Barr Virus), tumor proteins derived from non-primary open reading frame mRNA sequences (Y-ESO1, LAGE1), Melan A, MART-1, MAGE-1, MAGE-3, BAGE, GAGE-1, GAGE-2, tyrosinase, gp100, gp75, HER-2/neu, c-erb-B2, EGFR, CEA, PSA, MUC-1, CA-125, Stn, TAG-72, KSA (17-1A; EPCAM), PSMA, p53 (point mutated and/or overexpressed), RAS (point mutated), HER-1/EGFR, calcitonin, cancer antigen 19-9, cancer antigen 125, alpha-fetoprotein, S-100 antigen, TA-90, antigen, VEGF, GD2, GM2, GD3, Anti-Id, CD20, CD19, CD22, CD36, Aberrant class II, B1, CD25 (IL-2R) (anti-TAC), or HPV. Metal nanoparticle-associated antibodies are useful, e.g., to direct and localize nanoparticles to a therapeutic target (e.g., a tumor) or an analyte ex vivo. In one embodiment, the antibody is a humanized antibody.

In other embodiments, the metal nanoparticles are functionalized with a stealth group, e.g., polyethylene glycol (PEG), a PEG derivative, a poly(amino)acid, e.g., poly(hydroxy-L-asparagine (Romberg et al. (2007), Biochim Biophys Acta, 1768(3):737-743, a carbohydrate, or a polypeptide.

In other embodiments, the metal nanoparticles are functionalized with a thermophilic enzyme.

In one embodiment, the therapeutic target is provided metal nanoparticles that are are functionalized with a thermophilic enzyme that has significant activity only at supraphysiological temperatures (e.g., 60-85° C.). The therapeutic target is subsequently exposed to a dose of infrared radiation to increase the temperature of the therapeutic target in the presence of a substrate for the metal nanoparticle-bound thermophilic enzyme. For example, the thermophilic enzyme (e.g., β-galactosidase from *Thermotoga maritima* can be used in conjunction with, e.g., an anti-cancer pro-drug such as galactose-geldaymycin. See Cheng et al. (2005), *J. Med. Chem.*, 48(2):645-652. Thus, conversion of the cancer pro-drug by the thermophilic enzyme will be localized to regions of elevated temperature within the therapeutic target. Accordingly, cells in a therapeutic target tissue can be killed either directly by heat ablation or indirectly by heat-driven enzymatic conversion of a pro-drug into an active cytotoxic agent. In some embodiments, the activated agent or enzyme can be used to locally produce or modulate other biological or chemical effects. For example, thermophilic, fibrinolytic enzymes, e.g., subtilisin, can dissolve blood clots, or other enzymes can be activated to break down inflammatory tissue, atherosclerotic plaque, neurofibrillary tangles, plaque associated with Alzheimer's and neurodegenerative or other diseases, enzymatic fat catabolism to reduce obesity and atheromas, metalloproteinases to break down cell barriers, or enzymes to accelerate chemical processes.

It is also possible to make use of a metal nanoparticle-linked thermophilic enzyme in combination with a marker substrate to transiently activate the substrate during infrared heating of nanoparticle aggregates and thereby "mark" cells in a therapeutic target (e.g., a tumor). This is useful, e.g., to track cells that "escape" from a therapeutic target (i.e., even after treatment) as can occur in, e.g., metastasis of a tumor. For example, the β-galactosidase substrate 2-Fluoro-4-nitrophenol-beta-D-galactopyranoside has been used to track cells expressing β-galactosidase in vivo by magnetic resonance imaging. See Kodibagkar et al. (2006), *Mag. Res. Im.*, 24(7): 959-962. The in vivo β-galactosidase substrate, DDAOG, a conjugate of beta-galactoside and 7-hydroxy-9H-(1,3-dichloro-9,9-dimethylacridin-2-one) (DDAO), has been used to image β-galactosidase-expressing glioma cells in vivo by far red fluorescence imaging. See Tung et al. (2004), *Cancer Res.*, 64(5):1579-1583.

A wide variety of thermophilic enzymes are known in the art. See, e.g., Vielle et al. (2001), *Microb. And Mol*. Suitable thermophilic enzymes include, but are not limited to, thermophilic alkaline phosphatases (e.g., from *T. neapolitana*), β-galactosidases (e.g., from *T. maritima*), proteases (e.g., WF146 protease), endoglucanases (e.g., from *T. maritima*), or DNA polymerases (e.g., Taq polymerase). Metal nanoparticle-associated thermophilic enzymes are useful, e.g., for heat-dependent enzymatic conversion of a pro-drug (e.g., galactose-geldanamycin conjugates) within or in close proximity to a therapeutic target.

In further embodiments, the metal nanoparticles are functionalized with a thermosensitive liposome. Thermosensitive liposomes as referred to herein undergo a gel-to-liquid crystalline phase transition at a temperatures higher than normal human physiological temperatures, e.g., temperatures from about 38° C. to about 45° C.), and thereby release any solutes (e.g., an anti-cancer agent) entrapped within the liposome into the surrounding solution. Thus, infrared heating of aggregates of metal nanoparticles having bound thermosensitive liposomes can be used to locally release therapeutic agents contained in the thermosensitive liposomes. Examples of thermosensitive liposomes, their synthesis, and their use are described in, e.g., U.S. Pat. Nos. 6,200,598, 6,623,430, and 6,690,976.

In some embodiments, the thermosensitive liposomes contain an anti-cancer agent, e.g., a radiosensitizer agent such as, 5-Iododeoxyunridine, cisplatin, or Efaproxiral.

In other embodiments, the thermosensitive liposomes contain a nucleic acid, e.g., a single or double stranded oligonucleotide. For example the oligonucleotides can be antisense or RNAi molecules. In one embodiment, the thermosensitive liposome contains anti-angiogenic RNAi molecules. For example, the anti-angiogenic RNAi can be an anti-VEGF RNAi as described in, e.g., U.S. Pat. No. 7,148,342 or in U.S. patent application Ser. No. 11/340,080. In further embodiments, the thermosensitive liposomes contain a polypeptide. For example the polypeptide can be a protein having thrombolytic activity such as, reteplase (r-PA or Retavase), alteplase (t-PA or Activase), urokinase (Abbokinase), prourokinase, anisoylated purified streptokinase activator complex (APSAC), and streptokinase.

In yet other embodiments, the thermosensitive liposomes contain, a fluorophore, preferably an infrared fluorophore. Localized release of the flurophore from thermosensitive liposomes in vivo (e.g., within a tumor) can be used to label cells at a particular site and point in time to subsequently track their location in vivo. For example, tumor cells or clusters of tumor cells that are fluorescently "tagged" at time of a treatment, but survive the treatment can be tracked should they metastasize to other regions. Many suitable fluorophores are known in the art. See, e.g., "The Handbook—A Guide to Fluorescent Probes and Labeling Technologies," Molecular Probes, Inc., Eugene, Oreg., (2004). For example, polypeptides can be labeled with one or more of the following fluorophores: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, phycoerythrin (B—, R—, or cyanine-), allophycocyanin, Oregon Green™, Cascade™ blue acetylazide, Alexa Fluor Dyes™ (Molecular Probes, Inc., Eugene, Oreg.), cyanine dyes, e.g. Cy3™, Cy5™ and Cy7™ dyes (Amersham Biosciences, UK, LTD), and near infrared cyanine fluorochromes as described in Lin et al. (2002), *Bioconjugate Chem.*, 13:605-610. In one embodiment, the fluorophore is IR-786. See Flaumenhaft et al. (2007), *Circulation*, 115(1):84-93. In another embodiment the fluorophore is IR-Dye78. See Zaheer et al. (2002), *Mol. Imaging*, 1(4):354-364. See also U.S. patent application Ser. No. 11/149,602.

Combination Treatments

The metal nanoparticle compositions described herein can also be used in combination with other therapeutic reagents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

In any case, the multiple therapeutic agents (one of which is a metal nanoparticle described herein) may be administered in any order or even simultaneously. If administered simultaneously, the multiple therapeutic agents may be provided in a single, unified form, or in multiple forms (by way of example only, either as a single injection or as two separate injections). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations is also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

In addition, the therapeutic agents described herein also may be used in combination with procedures that may provide additional or synergistic benefit to the patient. In one embodiment, nanoparticle-mediated hyperthermia is used in combination with photodynamic therapy to treat the therapeutic target. In another embodiment, nanoparticle-mediated hyperthermia is used in combination with radiotherapy to treat the therapeutic target.

The metal nanoparticle compositions described herein and combination therapies can be administered before, during or after the occurrence of a disease or condition associated with a therapeutic target (e.g., a blood clot), and the timing of administering the metal nanoparticle composition can vary. Thus, for example, the compositions can be administered to a subject during or as soon as possible after the onset of the condition. The administration of the metal nanoparticle compositions or co-agent can be initiated within the first 48 hours of the onset of the symptoms or diagnosis of a condition associated with a therapeutic target, preferably within the first 48 hours of the onset of the symptoms or of the diagnosis, more preferably within the first 6 hours of the onset of the symptoms or of the diagnosis, and most preferably within 3 hours of the onset of the symptoms or of the diagnosis.

Anti-Cancer Agents

Where the subject is suffering from a tumor, a metal nanoparticle composition can be used in any combination with one or more anti-cancer agents (including, e.g., radiosensitizers) or any pro-drugs thereof Examples of anti-cancer agents include, but are not limited to, any of the following and pro-drugs thereof: 5-aza-2'-deoxycytidine, all trans retinoic acid, doxorubicin, vincristine, etoposide, gemcitabine, imatinib (Gleevec®), 17-N-Allylamino-17-Demethoxygeldanamycin (17-AAG), flavopiridol, LY294002, bortezomib, trastuzumab, BAY 11-7082, PKC412, or PD184352.

Taxol™, also referred to as "paclitaxel", which is an anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with metal particle compositions described herein.

Other anti-cancer agents that can be employed in combination with metal nanoparticles include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with metal nanoparticles include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with metal nanoparticles include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with metal nanoparticles include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination with metal nanoparticles include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful in combination with metal nanoparticles include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with metal nanoparticles include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCI), AC-7700 (Ajinomoto, also known as AVE-8062, AVE-8062A, CS-39-L-Ser.HCI, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Photosensitizing Agents (Photosensitizers)

Photosensitizers are molecules capable of the photochemical conversion of an irradiating energy into radical and cytotoxic species, which in turn mediates the desired effect on a therapeutic target ("photodynamic therapy"). Examples of photosensitizers and their use include, e.g., U.S. patent application Ser. No. 10/615,275. In some embodiments the metal nanoparticles described herein are conjugated to a photosensitizer, e.g., by a photocleavable linker.

When employing photodynamic therapy, a target area is treated with light at about 732±16.5 nm (full width at half max) delivered by an LED device or an equivalent light source (e.g., a solid state diode laser) at an intensity of about 5-150 mW/cm2 for a total light dose of 0.5-600 J/cm2.

After the photosensitizer-bearing metal nanoparticles have been administered, the therapeutic target is photoirradiated at a wavelength similar to the absorbance of the photosensitizer, usually either about 400-500 nm or about 700-800 nm, more preferably about 450-500 nm or about 710-760 nm, or most preferably about 450-500 nm or about 725-740 nm. The light source may be a laser, a light-emitting diode, or filtered light from, for example, a xenon lamp; and the light may be administered topically, endoscopically, or interstitially (via, e.g., a fiber optic probe), or intraarterially. The fluence and irradiance during the photoirradiating treatment can vary depending on type of tissue, depth of target tissue, and the amount of overlying fluid or blood. For example, a total light energy of about 100 J/cm$^2$ can be delivered at a power of 200 mW to 250 mW, depending upon the therapeutic target.

Examples of photosensitizers useful for the described methods include, but are not limited to, the following naturally occurring or synthetic compounds and derivatives thereof: pyrrole derived macrocyclic compounds, porphyrins, chlorins, bacteriochlorins, isobacteriochlorins, phthalocyanines, naphthalocyanines, porphycenes, porphycyanines, pentaphyrins, sapphyrins, benzochlorins, chlorophylls, azaporphyrins, the metabolic porphyrinic precursor 5-amino levulinic acid, PHOTOFRIN®, synthetic diporphyrins and dichlorins, phenyl-substituted tetraphenyl porphyrins (e.g., FOSCAN™. picket fence porphyrins), indium chloride methyl pyropheophorbide (MV64013™), 3,1-meso tetrakis (o-propionamido phenyl)porphyrin, verdins, purpurins (e.g., tin and zinc derivatives of octaethylpurpurin (NT2), and etiopurpurin (ET2)), zinc naphthalocyanines, anthracenediones, anthrapyrazoles, aminoanthraquinone, phenoxazine dyes, chlorins (e.g., chlorin e6, and mono-1-aspartyl derivative of chlorin e6), benzoporphyrin derivatives (BPD) (e.g., benzoporphyrin monoacid derivatives, tetracyanoethylene adducts of benzoporphyrin, dimethyl acetylenedicarboxylate adducts of benzoporphyrin, Diels-Adler adducts, and monoacid ring "a" derivative of benzoporphyrin), low density lipoprotein mediated localization parameters similar to those observed with hematoporphyrin derivative (HPD), sulfonated aluminum phthalocyanine (Pc) (sulfonated A1Pc, disulfonated (A1PcS.sub.2), tetrasulfonated derivative, sulfonated aluminum naphthalocyanines, chloroaluminum sulfonated phthalocyanine (CASP)), phenothiazine derivatives, chalcogenapyrylium dyes cationic selena and tellurapyrylium derivatives, ring-substituted cationic phthalocyanines, pheophorbide alpha, hydroporphyrins (e.g., chlorins and bacteriochlorins of the tetra(hydroxyphenyl) porphyrin series), phthalocyanines, hematoporphyrin (HP), protoporphyrin, uroporphyrin III, coproporphyrin III, protoporphyrin IX, 5-amino levulinic acid, pyrromethane boron difluorides, indocyanine green, zinc phthalocyanine, dihematoporphyrin, benzoporphyrin derivatives, carotenoporphyrins, hematoporphyrin and porphyrin derivatives, rose bengal, bacteriochlorin A, epigallocatechin, epicatechin derivatives, hypocrellin B, urocanic acid, indoleacrylic acid, rhodium complexes, etiobenzochlorins, octaethylbenzochlorins, sulfonated Pc-naphthalocyanine, silicon naphthalocyanines, chloroaluminum sulfonated phthalocyanine, phthalocyanine derivatives, iminium salt benzochlorins, and other iminium salt complexes, Merocyanin 540, Hoechst 33258, and other DNA-binding fluorochromes, psoralens, acridine compounds, suprofen, tiaprofenic acid, non-steroidal anti-inflammatory drugs, methylpheophorbide-a-(hexyl-ether), and other pheophorbides, furocoumarin hydroperoxides, Victoria blue BO, methylene blue, toluidine blue, porphycene compounds described in U.S. Pat. No. 5,179,120, indocyanines, and any combination of any or all of the above.

Thrombolytic Agents

Where the subject is in need of thrombolysis, a metal nanoparticle composition can be used in any combination with one or more thrombolytic agents including, but not limited to, reteplase (r-PA or Retavase), alteplase (t-PA or Activase), urokinase (Abbokinase), prourokinase, anisoylated purified streptokinase activator complex (APSAC), and streptokinase.

Ionizing Radiation

Where the subject is suffering from a neoplastic tissue (e.g., a tumor), metal nanoparticle-mediated hyperthermia can be used in combination with ionizing radiation (e.g., X-ray, γ-ray, alpha particle, or neutron beam irradiation). The amount of ionizing radiation needed depends upon the nature of the neoplastic tissue. Means for determining an effective amount of radiation are well known in the art. When used in combination with hyperthermia, effective doses of ionizing radiation are lower and thereby reduce the deleterious side effects associated with higher doses of ionizing radiation.

Pharmaceutical Formulations of Metal Nanoparticle Compositions

Pharmaceutical compositions that include the metal nanoparticles described herein may be formulated in a conventional manner using one or more physiologically acceptable carriers including excipients and auxiliaries which facilitate processing of the metal nanoparticles into preparations which can be used pharmaceutically. Proper formulation is dependent upon the route of administration chosen. Well-known techniques, carriers, and excipients may be used as suitable and as understood in the art. A summary of pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety.

Provided herein are pharmaceutical compositions that include metal nanoparticles described herein, and a pharmaceutically acceptable, isotonicity agent(s), diluent(s), excipient(s), or carrier(s). In addition, the metal nanoparticles described herein can be administered as pharmaceutical compositions in which the metal nanoparticles are mixed with other active ingredients, as in combination therapy. In some embodiments, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions can also contain other therapeutically or diagnostically valuable substances such as anti-cancer agents, anti-inflammatory agents, thrombolytic agents, prodrugs, or in vivo enzyme marker substrates (e.g., 2-Fluoro-4-nitrophenol-beta-D-galactopyranoside).

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In other embodiments, compositions may also include one or more isotonicity agents, such as dextrose, mannitol, or lactose.

A pharmaceutical composition, as used herein, refers to a mixture of metal nanoparticles described herein, with other chemical components, such as carriers, stabilizers, diluents, dispersing agents, suspending agents, thickening agents, and/or excipients. The pharmaceutical composition facilitates providing metal nanoparticles to a therapeutic target. In practicing the methods of treatment or use provided herein, therapeutically effective amounts of metal nanoparticles described herein are administered in a pharmaceutical composition to a subject having a disease, disorder, or condition to be treated. Preferably, the subject is a human. A therapeutically effective amount can vary widely depending on the severity of the disease, the age and relative health of the subject, the physical characteristics of the metal nanoparticles used, and other factors. The metal nanoparticles described herein can be used alone or in combination with one or more therapeutic agents as components of mixtures.

The pharmaceutical formulations described herein can be administered to a subject by multiple administration routes, including parenteral (e.g., intravenous, subcutaneous, intramuscular), topical, rectal, or transdermal administration routes. The pharmaceutical formulations described herein include, but are not limited to, aqueous liquid dispersions, self-emulsifying dispersions, solid solutions, liposomal dispersions, or solid dosage forms.

The pharmaceutical compositions will include at least one metal nanoparticle described herein, such as, for example, a gold nanoparticle functionalized with with anti-tumor antigen antibody.

The compositions described herein can be formulated for administration to a subject via any conventional means including, but not limited to, oral, parenteral (e.g., intravenous, subcutaneous, or intramuscular), buccal, intranasal, rectal or transdermal administration routes.

Formulations that include metal nanoparticles, suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethyleneglycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonicity agents, such as sugars (e.g., dextrose), mannitol, sodium chloride, and the like.

For intravenous injections, metal nanoparticle compositions described herein may be formulated in aqueous solutions, preferably in physiologically compatible buffers such as Hank's solution, Ringer's solution, or physiological saline buffer along with an isotonicity agent (e.g., dextrose, mannitol, or lactose).

For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical compositions described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the metal nanoparticles in water-soluble form. Additionally, suspensions of the metal nanoparticles may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the metal nanoparticles to allow for the preparation of highly concentrated solutions. Alternatively, the active ingredient may be in powder form for constitution with a suitable vehicle, e.g., sterile pyrogen-free water, before use.

Methods of Dosing and Treatment Regimens

The metal nanoparticle compositions described herein can be used in the preparation of medicaments for increasing the infrared absorptivity of a therapeutic target, or for the treatment of diseases or conditions that would benefit, at least in part, from increased infrared absorptivity of the therapeutic target. In addition, a method for treating any of the diseases or conditions described herein in a subject in need of such treatment, involves administration of pharmaceutical compositions containing metal nanoparticles described herein in therapeutically effective amounts to a therapeutic target in said subject.

The compositions containing the metal nanoparticles described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, therapeutic target characteristics such as shape, volume, tissue depth, infrared irradiation dosage, and other factors such as previous therapy, the patient's health status, weight, and response to compositions in combination with infrared irradiation, as well as the judgment of the treating physician. It is considered well within the skill of the art for one to determine therapeutically effective amounts of therapeutic agents by routine experimentation (including, but not limited to, a dose escalation clinical trial).

In prophylactic applications, compositions containing the metal nanoparticles described herein are administered to a patient susceptible to or otherwise at risk of a particular disease, disorder or condition associated with a therapeutic target. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In general, however, doses employed for adult human treatment will typically be in the range of 1-2000 mg/kg per administration, preferably 10-800 mg/kg per administration. The desired dose may conveniently be presented in a single dose or as divided doses administered simultaneously (or over a short period of time) or at appropriate intervals, for example as two, three, four or more sub-doses per day. In embodiments in which the nanoparticles are functionalized with a drug to be released or activated, the amount of the nanoparticle composition administered can be substantially less than that required for ablative tissue heating. For example, the dose can be 0.001-5 mg/kg. In other embodiments, where a combined pharmacological and thermal ablative effect is desired, intermediate dose ranges can be used.

The foregoing ranges are merely suggestive, as the number of variables in regard to an individual treatment regime is large, and considerable excursions from these recommended values are not uncommon. Such dosages may be altered depending on a number of variables, not limited to the absorptive properties of the metal nanoparticles used, the therapeutic target to be treated, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the LD50 (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and ED50. Metal nanoparticle compositions exhibiting high therapeutic indices are preferred. The data obtained from cell culture assays and animal studies can be used in formulating a range of dosage for use in human. The dosage of such compositions lies preferably within a range of circulating concentrations that include the ED50 with minimal toxicity. The dosage may vary within this range depending upon the dosage form employed and the route of administration utilized.

The compositions and methods described herein may also be used in conjunction with other well known therapeutic reagents that are selected for their particular usefulness against the condition that is being treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

In certain instances, it may be appropriate to administer metal nanoparticles described herein in combination with another therapeutic agent. By way of example only, the benefit experienced by a patient may be increased by administering one of the metal nanoparticle compositions described herein with another therapeutic agent (e.g., an anti-cancer agent). In any case, regardless of the disease, disorder or condition being treated, the overall benefit experienced by the patient may simply be additive of the two therapeutic agents or the patient may experience a synergistic benefit.

The particular choice of therapeutic agents used will depend upon the diagnosis of the attending physicians and their judgment of the condition of the patient and the appropriate treatment protocol. The therapeutic agents (e.g., a metal nanoparticle composition and an anti-cancer compound) may be administered concurrently (e.g., simultaneously, essentially simultaneously or within the same treatment protocol) or sequentially, depending upon the nature of the disease, disorder, or condition, the condition of the patient, and the actual choice of therapeutic agents used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically-effective dosages can vary when the therapeutic agents are used in treatment combinations. Methods for experimentally determining therapeutically-effective dosages of therapeutic agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compositions will of course vary depending on the type of co-agents employed, on the disease or condition being treated and so forth. In addition, when co-administered with one or more biologically active agents, the metal nanoparticles provided herein may be administered either simultaneously with the other biologically active agent(s), or sequentially. If administered sequentially, the attending physician will decide on the appropriate sequence of administering protein in combination with the biologically active agent (s).

In any case, the multiple therapeutic agents (one of which is a metal nanoparticle described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents. The use of multiple therapeutic combinations is also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic agent being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the metal nanoparticle compositions described herein also may be used in combination with procedures that may provide additional or synergistic benefit to the patient. By way of example only, patients are expected to find therapeutic and/or prophylactic benefit in the methods described herein, wherein pharmaceutical compositions of a metal nanoparticle disclosed herein and/or combinations with other therapeutics are combined with genetic testing to determine whether that individual is a carrier of a mutant gene that is known to be correlated with certain diseases or conditions.

The compositions described herein and combination therapies can be administered before, during or after the occurrence of a disease or condition, and the timing of administering the composition containing metal nanoparticles can vary. Thus, for example, the compositions can be used as a prophylactic in order to prevent the occurrence of a disease or condition associated with a therapeutic target. The compositions can be administered to a subject during or as soon as possible after the onset of symptoms or after diagnosis. For acute conditions, the administration of the compositions can be initiated within the first 48 hours of the onset of symptoms for acute conditions, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. Metal nanoparticle compositions are preferably administered as soon as is practicable after the onset of a disease or condition is detected or suspected, and for a length of time necessary for the treatment of the disease, such as, for example, either once or multiple treatments over about 5 days to about 6 months. The length of treatment can vary for each subject, and the length can be determined using the known criteria. For example, compositions containing the metal nanoparticles can be administered in combination with infrared radiation, repeatedly for at least 2 weeks, 1 month to about 5 years, or about 1 month to about 3 years.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Example 1

Gold Nanoparticles Have a High Infrared Aggregate Absorptivity Amplification Factor (A3F)

Figure 2:
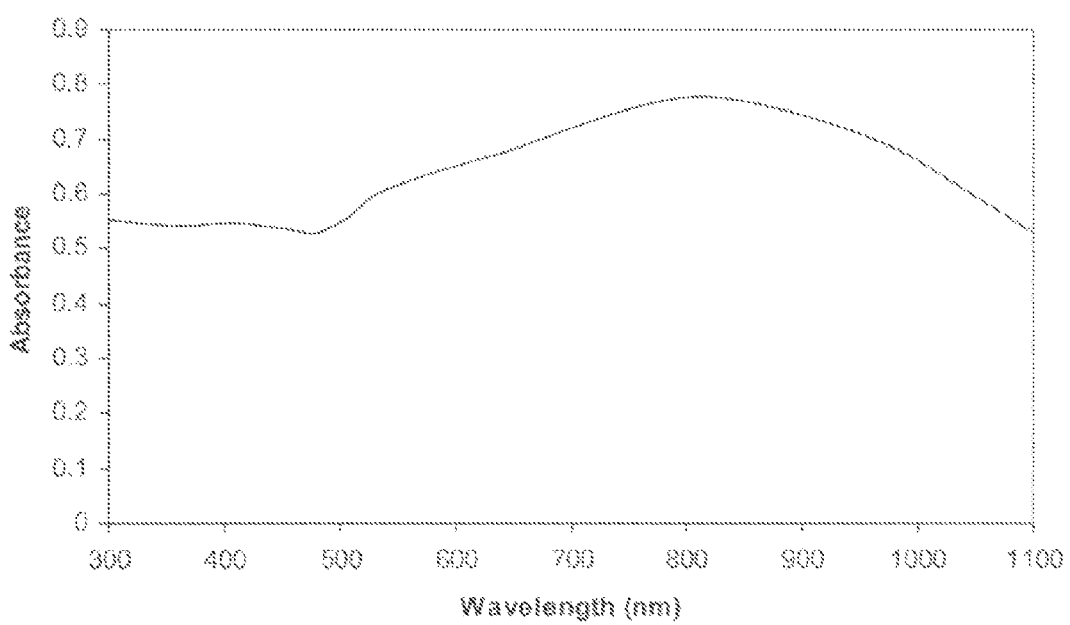
FIG. 2 is a representative absorbance spectrum of 15 nm gold nanoparticles, after aggregation in 0.3M NaCl, for wavelengths from 300-1100 nm.
Figure 3:
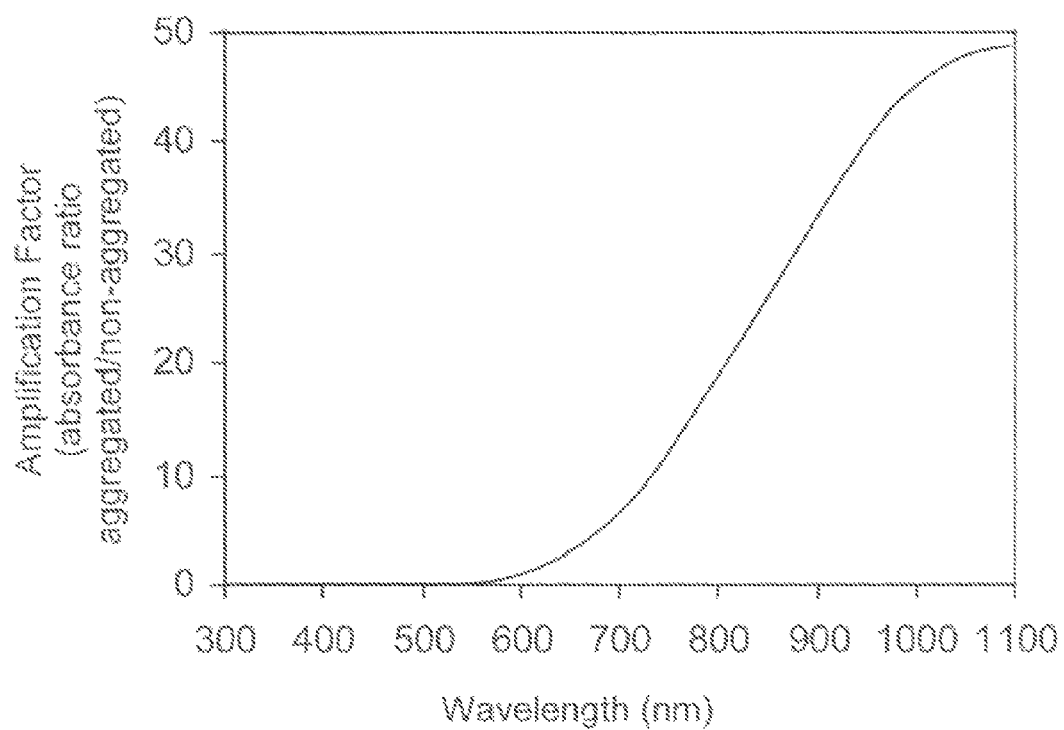
FIG. 3 is a representative graph showing the ratio of the absorbance spectrum for aggregated 15 nm gold nanoparticles to the absorbance spectrum for unaggregated 15 nm gold nanoparticles.

The infrared absorptivity of unaggregated vs aggregated 15 nm gold nanoparticles was determined as follows. 15 nm gold nanoparticles were prepared by boiling 100 ml 0.01% $HAuCl_4$, adding 3 ml of 1% sodium citrate, and then continuing the boiling for 15 minutes. A 1 mg/ml lipoic acid solution in ethanol was mixed with a 2 mg/ml solution of sodium borohydride in ethanol in a 3:1 volume ratio (lipoic acid: borohydride) and allowed to react for 20 min. Afterwards, 0.5 ml of the gold solution was added to 0.045 ml of the lipoic acid/borohydride solution. After 10 min, the coated gold nanoparticles were purified by precipitation in 1 M NaCl and centrifugation at 15,000×g for 30 seconds. The supernatant was removed and the gold nanoparticles were resuspended in deionized water. The absorption spectrum of the resuspended gold nanoparticles was then measured for wavelengths from 300-1100 nm, as shown in FIG. 1. Subsequently, the gold nanoparticles were aggregated aggregated with 300 mM NaCl. The 300-1100 absorbance spectrum was then remeasured, as shown in FIG. 2. By dividing the second (aggregated nanoparticle) absorbance spectrum by the first (unaggregated nanoparticle) spectrum, a profile of the A3F for each wavelength was obtained, which shows the fold absorption increase of aggregated vs unaggregated gold nanoparticles at each wavelength (FIG. 3). As shown in FIG. 3, aggregated 15 nm gold nanoparticles have an absorption at 800 nm and 1100 nm that is 19 fold and 48 fold higher, respectively, than the corresponding absorbance values for the unaggregated gold nanoparticles. In other words, the 15 nm gold nanoparticles had an $A3F_{800}=19$ and an $A3F_{1100}=48$.

Similar results were also obtained using 2 nm gold nanoparticles ($A3F_{800}=12.9$ and an $A3F_{1100}=23.3$; data not shown). Based on these data it was concluded that aggregated 15 and 2 nm gold nanoparticles had much higher infrared absorptivity than the corresponding unaggregated nanoparticles.

Example 2

Gold Nanoparticles Increase Infrared Absorptivity and Mediate Photothermal Ablation of a Tumor In view of the high infrared A3F of gold nanoparticles, we sought to determine their ability to selectively increase the infrared absorptivity of a therapeutic target in vivo. 15 nm gold nanoparticles were prepared by boiling 500 ml 0.01% $HAuCl_4$, adding 15 ml of 1% sodium citrate, and continuing the boiling for 20 minutes. Anti-carcinoembryonic antigen (CEA) antibody was prepared from a hybridoma and purified by ion exchange and gel filtration chromatography. The gold particles were coated with the the anti-CEA antibody by exposing them to a 3 µg/ml antibody solution and further passivating the gold surface by exposure to reduced lipoic acid. The gold particles were purified by centrifugation, filtered with a 0.2 micron filter, and shown to have good CEA binding activity as determined in a dot blot assay.

Figure 5:
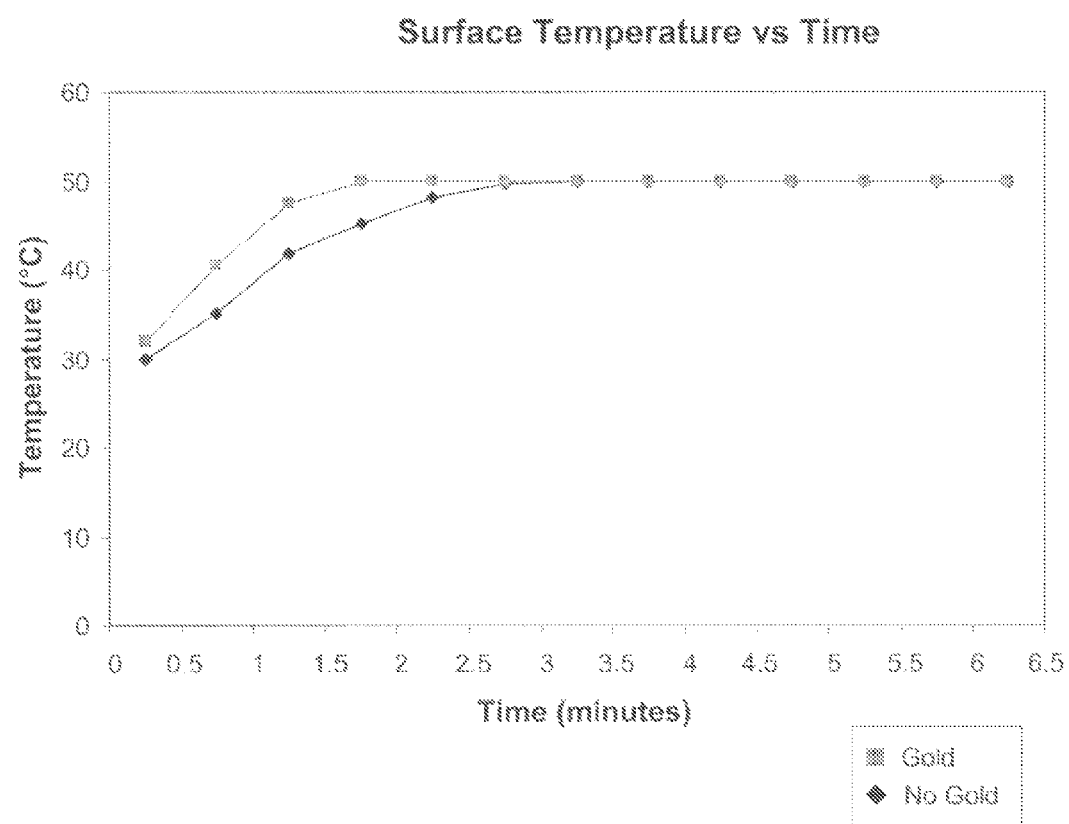
FIG. 5 is a representative graph showing the subcutaneous temperature over a tumor in a gold nanoparticle-injected mouse and a tumor in a control mouse (no gold nanoparticles administered) during infrared irradiation of each tumor.
Figure 6:
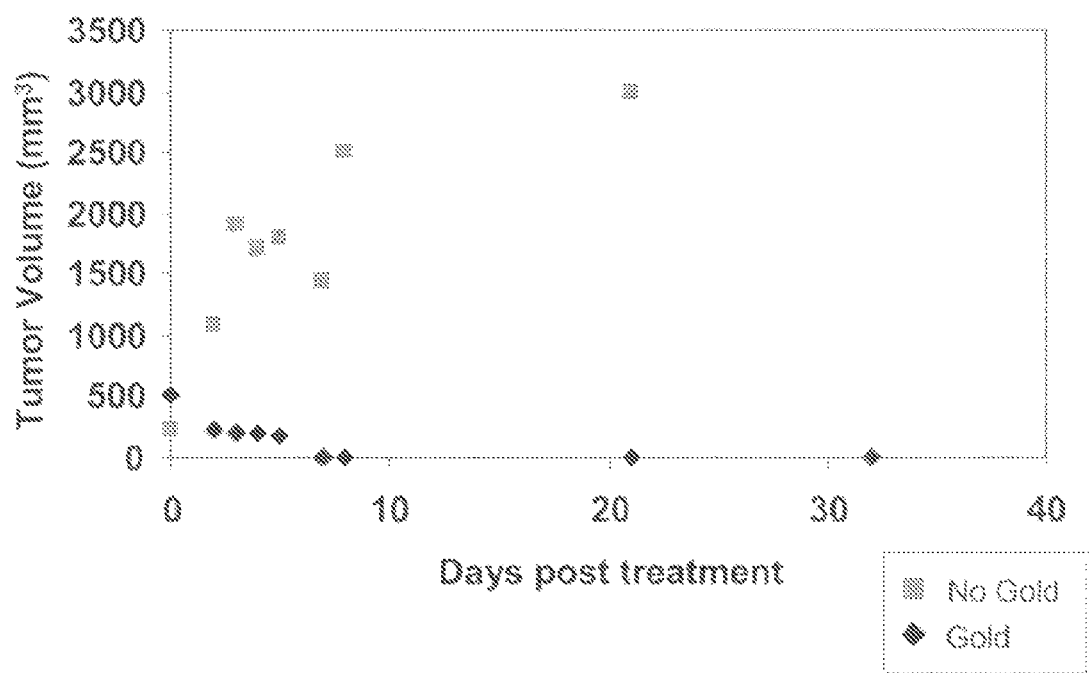
FIG. 6 is a representative graph showing a time course (day 0-day 32 post-treatment) of tumor volume in the control mouse and in the gold nanoparticle-treated mouse. Note that the control mouse died at day 21.

For a therapeutic test, 0.2 ml of the just-described gold nanoparticle solution at an $OD_{520}=1000$ was injected into a nude mouse bearing an implanted LS174 human tumor cell colon carcinoma in its leg (FIG. 4, top left panel). A control animal did not receive a gold injection (not shown). Approximately 2.5 hours after injection, the tumor was purple in color, with no obvious coloration in immediately surrounding tissue (FIG. 4, top right panel). A one inch circular mask was then positioned over the tumor to limit the area irradiated. The animal was irradiated with a water filtered infrared lamp from Hydrosun (Hydrosun Medizintechnik, Müllheim, Germany) at a dose rate of 2 watts/cm$^2$ (FIG. 4, bottom panel). A small thermocouple had been placed subcutaneously in the center of the tumor to monitor the surface temperature and avoid skin burns. When this temperature reached 50° C., the lamp was turned off and it was cycled on and off to maintain the temperature at 50° C. The total treatment time was six minutes. As shown in FIG. 5, the animal without gold nanoparticles was treated similarly, but it was found that the surface temperature took longer to reach 50° C., and during the six minutes the lamp was on for a longer time to maintain 50° C. For the animal treated with gold nanoparticles ("gold-treated animal"), the total infrared exposure time was 3.2 minutes, for a total irradiation dose of 1860 Joules. For the control animal, the total infrared exposure time was 4.9 min, for a total dose of 2890 Joules. Thus, the control animal actually received 55% more infrared irradiation than the gold nanoparticle-injected animal.

Subsequently, one day after treatment the tumor on the gold-treated animal became black and blue with a reddish erythema around the periphery. The tumor in the control animal did not show this change. On the second day post-treatment the tumor in the gold-treated animal turned black, an apparent consequence of thrombosis and necrosis. In contrast, little change was observed in the tumor of the control animal. In the following days, the tumor in the gold-treated animal was resorbed with a scab developing then disappearing. Surprisingly, the leg in the gold-treated animal showed no functional damage. On the contrary, the leg was limber and strong. In the control animal, a darkened area where the infrared lamp was the closest to the tumor appeared three days post-treatment, and got larger by five days, but the tumor continued to grow. In addition, seven days post treatment, the control-animal tumor not only grew in size, but also developed an ulceration in its center, which subsequently expanded. Eight days post treatment, the no-gold animal had abnormal black feces indicating occult internal bleeding. This animal died 21 days post treatment. The animal receiving gold fully recovered and was healthy (see FIG. 7)). The animal did not display any abnormal behavior.

Based on these data, it was concluded that the administered gold nanoparticles very effectively increased the infrared absorptivity of a tumor and thereby mediated its ablation by infrared irradiation. In contrast, in the control animal, mere irradiation of a tumor with an even greater amount of infrared irradiation failed to arrest its growth.

Example 3

Treatment of Tumors in Mice Using IR and 2 nm Gold Nanoparticles

Figure 8:
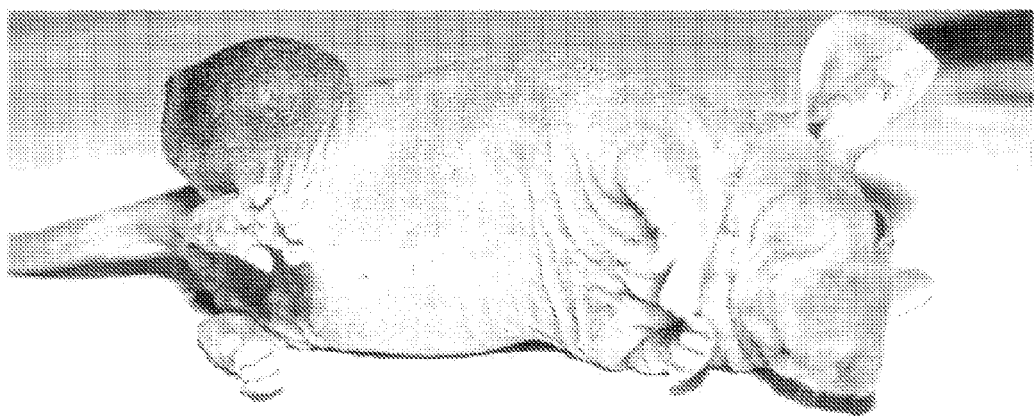
FIG. 8 is a representative photograph of a nude mouse, bearing a human colon tumor xenograft, two hours after injection of 2 nm gold nanoparticles into the tail vein. Note the localization of the gold nanoparticles in the human colon tumor xenograft on the hindleg and the intense darkening resulting from clustering of the nanoparticles, thus increasing their absorbance.
Figure 11:
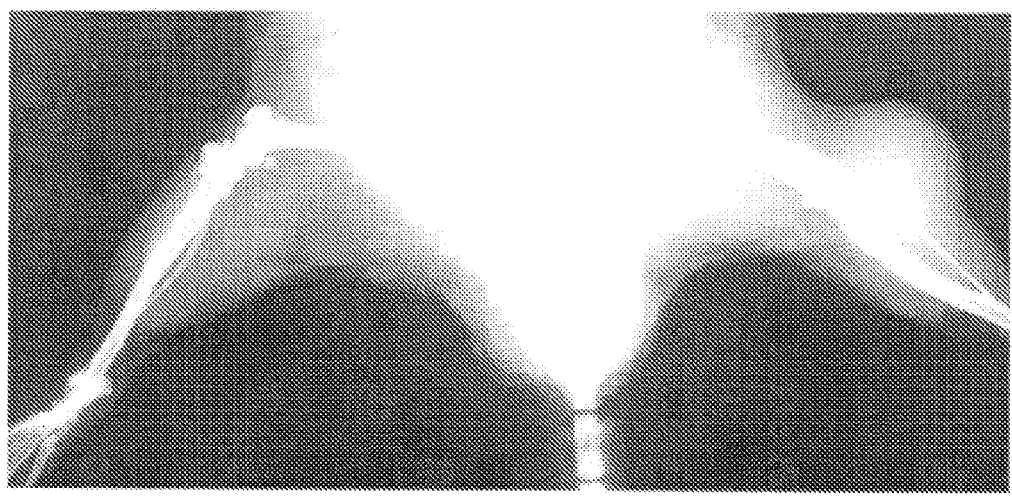
FIG. 11 is a representative X-ray planar radiogram of a nude mouse, bearing a subcutaneous human colon carcinoma xenograft in its leg, four hours after injection with anti-CEA-15 nm gold nanoparticles. The tumor shows up with high intensity (lump on leg on right side of image).

Nude mice with human colon cancer xenografts in their hindlegs were injected intravenously in the tail vein with a solution of 2 nm gold nanoparticles (2.3 g Au/kg) in phosphate buffered saline. After two hours, the nanoparticles had not only accumulated specifically in the tumor, but exhibited clustering resulting in a darker coloration, as shown in FIG. 8.

Infrared treatment was applied as described in Example 2, and the tumors were successfully specifically ablated by this treatment.

Thus, it was concluded that that the large bioamplification effect in absorption observed with 2 nm gold nanoparticles can be used to both identify and treat tumors.

Example 4

Uptake of Antibody-Labeled Gold Nanoparticles In Vitro

A study was conducted to examine the uptake of antibody-labeled gold nanoparticles in vitro. The hybridoma expressing MAb225 to EGFR was cultured and the secreted antibody was purified using a protein A chromatography. 15 nm gold-antibody conjugates were made and purified by centrifugation. A431 cells, which highly express EGFR, and a cell line with low expression, MCF7, were cultured and incubated with gold nanoparticle-antibody conjugates. The uptake of the conjugates in the A431 cells was obvious after one day, as a cell pellet was observed to be black, and examination under the light microscope of washed cells revealed visible black dots in the cytoplasm (FIG. 8, bottom panel), but were absent in A431 cells not incubated with the gold nanoparticles (FIG. 8, top panel). In contrast, MCF7 did not show such nanoparticle uptake (data not shown). No differences in cell growth were observed between cells exposed to and not exposed to gold. Based on this evidence, it was concluded that antibody-gold nanoparticles were selectively taken up and clustered in cells expressing EFGR, without toxicity.

Example 5

Synergy of Hyperthermia and Radiotherapy

A study was conducted to evaluate the efficacy of treating squamous cell carcinoma by combining hyperthermia and radiotherapy. Using squamous cell carcinoma (SCC)VII cell line tumors implanted in the hindleg of C3H mice, the leg was submerged in a water bath at 44° C. for 20 min. This control treatment was found to have no debilitating effect on its own. However, this treatment had little effect on tumor growth rate (FIG. 9, top panel), and all animals died of tumor overgrowth.

In another control treatment, radiation alone (157 kVp, 30Gy), was found to slow tumor growth, but ultimately all animals succumbed except one by 81 days (FIG. 9, middle panel). On the other hand, when when these two regimens were combined (heating just before irradiation), all tumors were found to shrink and the mice survived through the latest time point in the study (81 days), as shown in FIG. 9 (bottom panel).

Thus, based on these data, it was concluded that combined hyperthermia and radiation therapy was effective for treating tumors. Further it was concluded that combining tumor-specific nanoparticle-IR heating with radiotherapy could be even more effective for treating a tumor effectively while minimizing radiation damage to surrounding tissues.

Example 6

X-Ray Imaging of Gold Nanoparticle Aggregates in a Tumor

X-ray detection of tumors by gold nanoparticle localization was evaluated. A mammography unit operating at 22 kVp was used to take an X-ray planar image of a nude mouse with a subcutaneous human colon carcinoma xenograft in leg 4 hours after injection with anti-CEA-15 nm gold nanoparticles. As shown in FIG. 10, a tumor, approximately 5 mm in size, showed up with high intensity (lump on leg on right side of image). Tumor intensity was not due to thickness of the tissue, as the thickness of the tumor was the same thickness as the leg muscle on the contralateral leg. Thus, it was concluded that gold nanoparticle localization in tumors can serve as a very useful contrast method for X-ray detection of tumors, particularly early on when the tumors are very small and difficult to detect by conventional X-ray radiography. Further, the sensitivity of the method could be much higher if difference images were taken before and after injection of the gold nanoparticles.

Example 7

Heating Caused by Aggregated Nanoparticles

A 27 gauge thermocouple wire was suspended in air and registered the ambient temperature of 22° C. It was then exposed to 1 W/cm$^2$ infrared from a continuous wave 810 nm laser source. The wire heated quickly and stabilized (due to air convection) to a temperature of 37° C. within 10 seconds which did not change over the course of 5 minutes. Subsequently, $6 \times 10^{-12}$ moles of 15 nm gold nanoparticles were aggregated and deposited on the wire. Without irradiation, the temperature reading was also the ambient, 22° C. Upon exposure to 1 W/cm$^2$ infrared from the continuous wave 810 nm laser source, the wire heated quickly and stabilized at 67° C. within 10 seconds and did not change over the course of 5 minutes. The volume of fluid that produced the aggregated particles was 167 microliters with a concentration of gold 0.05% gold by weight. Since tumor delivery of gold can be 0.5% or higher, this incremental heating of 30° C. could be much higher in tumor tissue, but even at this level would rapidly result in cellular necrosis, coagulation, or other severe hyperthermia effects.

Example 8

Infrared Aggregate Absorptivity Amplification Factor (A3F) of Gold Nanoparticles with Thin Shells A 0.05 mg Au/ml solution of 15 nm gold nanoparticles, made by reduction with trisodium citrate resulting in a thin counterion shell, was placed in a spectrophotometer that collected a large fraction of the off-axis scattered light by use of a mirrored off-axis cavity (Sim Aminco DN2000 UV Vis spectrophotometer, SLM Instruments Inc.) thus compensating for and eliminating to some degree the scattering component. The extinction at 800 nm was measured to be 0.014 optical density units (OD). The particles were then aggregated by adjusting the solution to 0.3 M NaCl and the extinction at 800 nm increased to 0.529 OD. This yielded an aggregate absorptivity amplification factor (A3F) of 37.8 at 800 nm. A thinner shell apparently permitted the gold particles to approach each other more closely, thus increasing the A3F.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a subject suffering from a therapeutic target, comprising providing a therapeutically effective plurality of nanoparticles to the therapeutic target in the subject and irradiating the therapeutic target with a therapeutically effective dose of infrared radiation, wherein:

(a) each of the cores of the nanoparticles consisting essentially of solid gold;
(b) the average effective diameter of the nanoparticles is between about 0.8 nm and 20 nm;
(c) the plurality of nanoparticles has an aggregate absorptivity amplification factor of at least about 3 to about 50, relative to unaggregated nanoparticles, for infrared wavelength irradiation; and
(d) the dose of infrared-wavelength radiation is sufficient to elevate a temperature within the therapeutic target to at least 42° C.

2. The method of claim 1, wherein at least about 50% of the nanoparticles in the plurality have effective diameters between about 5 to about 20 nm.

3. The method of claim 2, wherein at least about 50% of the nanoparticles in the plurality have effective diameters between about 10 to about 20 nm.

4. The method of claim 1, wherein at least about 10% of the nanoparticles in the plurality have an aggregate absorptivity amplification factor of at least about 20 to about 50, relative to unaggregated nanoparticles, for infrared wavelength irradiation.

5. The method of claim 1, wherein at least about 50% of the nanoparticles in the plurality have an aggregate absorptivity amplification factor, relative to unaggregated nanoparticles, of at least about 20 to about 50 for infrared wavelength irradiation.

6. The method of claim 1, wherein the therapeutic target is a tumor.

7. The method of claim 6, wherein the tumor is a solid tumor.

8. The method of claim 7, wherein the plurality of nanoparticles is provided by direct infusion into the tumor.

9. The method of claim 8, wherein the tumor contains vasculature that permits extravasation.

10. The method of claim 1, wherein the plurality of nanoparticles is provided by parenteral administration to the subject.

11. The method of claim 1, further comprising waiting for a time sufficient to aggregate a portion of the plurality of nanoparticles in proximity of the tumor wherein said sufficient time is about 10 second to about 60 minutes.

12. The method of claim 7, wherein the temperature is sufficient to kill a plurality of cells in the tumor.

13. The method of claim 1, wherein the dose of infrared-wavelength radiation is sufficient to elevate the temperature within the therapeutic target to between about 42° C. to about 500° C.

14. The method of claim 1, wherein a portion of the plurality of nanoparticles have bound to them (i) an antibody; (ii) a stealth group; (iii) a thermophilic enzyme, (iv) a thermosensitive liposome containing a therapeutic agent, or (v) a therapeutic agent.

15. The method of claim 14, wherein a portion of the plurality of nanoparticles have an antibody bound to them.

16. The method of claim 15, wherein the antibody is specific to an antigen on the therapeutic target.

17. The method of claim 16, wherein the therapeutic target is a solid tumor.

18. The method of claim 14, wherein a portion of the plurality of nanoparticles have a stealth group bound to them.

* * * * *